(12) United States Patent
Fandke et al.

(10) Patent No.: US 7,183,085 B1
(45) Date of Patent: Feb. 27, 2007

(54) METHOD AND NUCLEIC ACIDS FOR DETERMINING THE PRESENCE OF MICRO-ORGANISMS SPECIFIC TO THE BREWING PROCESS

(75) Inventors: Markus Fandke, Berlin (DE); Alexander Gasch, Berlin (DE); Kornelia Berghof, Berlin (DE)

(73) Assignee: Biotecon Diagnostics GmbH, Berlin (DE)

( * ) Notice: Subject to any disclaimer, the term of this patent is extended or adjusted under 35 U.S.C. 154(b) by 425 days.

(21) Appl. No.: 10/088,666

(22) PCT Filed: Sep. 8, 2000

(86) PCT No.: PCT/EP00/08808

§ 371 (c)(1), (2), (4) Date: Jun. 28, 2002

(87) PCT Pub. No.: WO01/23605

PCT Pub. Date: Apr. 5, 2001

(30) Foreign Application Priority Data

Sep. 24, 1999 (DE) .................. 199 45 964

(51) Int. Cl.
*C12P 19/34* (2006.01)
(52) U.S. Cl. .......................... 435/91.2; 435/6
(58) Field of Classification Search .............. 435/6, 435/91.2
See application file for complete search history.

(56) References Cited

U.S. PATENT DOCUMENTS

| 5,484,909 A | * | 1/1996 | Nietupski et al. ........ 536/24.32 |
| 5,705,339 A | | 1/1998 | Nietupski et al. |
| 5,738,993 A | * | 4/1998 | Fugono et al. ................ 435/6 |
| 5,744,311 A | * | 4/1998 | Fraiser et al. ................. 435/6 |
| 5,792,607 A | * | 8/1998 | Backman et al. .............. 435/6 |
| 5,869,642 A | | 2/1999 | Sakamoto |

FOREIGN PATENT DOCUMENTS

| DE | 690 22 180 T2 | 2/1996 |
| DE | 690 30 131 T2 | 7/1997 |
| DE | 196 16 750 A1 | 11/1997 |
| JP | 6-141899 | * 5/1994 |
| WO | WO 99/22023 A2 | 5/1999 |

OTHER PUBLICATIONS

Satokari et al. (Internation Journal of Food Microbiology 45(1998) 119-127).*
DiMichelle et al., *J. Am. Soc. Brew. Chem.*, 51 (2), 63-66 (1993).
Doyle et al., *J. Ind. Microbiol.*, 15 (2), 67-70 (1995).
Ludwig et al., *Database Genbank*, Database Accession No. X68423 (Mar. 29, 1993).
Ludwig et al., *Database Genbank*, Database Accession No. X68426 (Mar. 29, 1993).
Mori et al., *Int. J. Syst. Bacteriol.*, 47 (1), 54-57 (1997).
Nagashima et al., *Database Genbank*, Database Accession No. D87678 (Feb. 7, 1999).
Patent Abstracts of Japan, 017 (278), (May 28, 1993) (JP 05 015400 A).
Satokari et al., *Int. J. Food Microbiol.*, 45, 119-127 (1998).
Stanier et al. (eds.), "The Microbial World," 5th Edition, Prentice Hall, New Jersey, USA, p. 326 (1986).
Van Der Meer et al., *Database Genbank*, Database Accession No. L08062 (Apr. 26, 1993).
Yap et al., *Database Genbank*, Database Accession No. AF116563 (Sep. 16, 1999).
Sequence Comparison between SEQ ID No. 21 from U.S. Patent No. 5,869,642 (A) and Genbank No. D87678, printed May 22, 2000.
Sequence Comparison between SEQ ID No. 104 and Genbank No. X68423, printed May 17, 2000.
Sequence Comparison between SEQ ID No. 1 and Genbank No. X68426, printed May 17, 2000.
Sequence Comparison between SEQ ID No. 2 and Genbank No. X68426, printed May 17, 2000.
Sequence Comparison between SEQ ID No. 3 and Genbank No. X68426, printed May 22, 2000.
Sequence Comparison between SEQ ID No. 4 and Genbank No. X68426, printed May 22, 2000.
Sequence Comparison between SEQ ID No. 5 and Genbank No. X68426, printed May 22, 2000.
Sequence Comparison between SEQ ID No. 6 and Genbank No. X68426, printed May 22, 2000.
Sequence Comparison between SEQ ID No. 7 and Genbank No. X68426, printed May 22, 2000.
Sequence Comparison between SEQ ID No. 8 and Genbank No. X68426, printed May 22, 2000.
Sequence Comparison between SEQ ID No. 9 and Genbank No. X68426, printed May 22, 2000.
Sequence Comparison between SEQ ID No. 10 and Genbank No. X68426, printed May 22, 2000.
Van Der Meer et al., *Database Genbank*, Database Accession No. L08062 (Apr. 26, 1993), printed May 17, 2000.
Sequence Comparison between Genbank No. X68426 and Genbank No. L08062, printed May 22, 2000.

(Continued)

*Primary Examiner*—Juliet C. Switzer
(74) *Attorney, Agent, or Firm*—Leydig, Voit & Mayer, Ltd.

(57) ABSTRACT

The invention relates to a method for the detection of *L. brevis*. The method comprises bringing the sample into contact with a combination of at least two first nucleic acid molecules, which hybridize with a *L. brevis* nucleic acid amplifying the *L. brevis* nucleic acid or a portion thereof to produce at least one amplification fragment; contacting the amplification fragments with at least one second nucleic acid molecule, which specifically hybridises with at least one amplification fragment that comprises a sequence of the *L. brevis* nucleic acid; and detecting at least one hybrid nucleic acid which consists of an amplification fragment and a second nucleic acid molecule.

5 Claims, No Drawings

OTHER PUBLICATIONS

Sequence Comparison between SEQ ID No. 11 and Genbank No. L08062, printed May 22, 2000.
Sequence Comparison between SEQ ID No. 12 and Genbank No. L08062, printed May 22, 2000.
Sequence Comparison between SEQ ID No. 13 and Genbank No. L08062, printed May 17, 2000.
Sequence Comparison between SEQ ID No. 14 and Genbank No. L08062, printed May 17, 2000.
Sequence Comparison between SEQ ID No. 17 and Genbank No. L08062, printed May 17, 2000.
Sequence Comparison between SEQ ID No. 18 and Genbank No. L08062, printed May 17, 2000.
Sequence Comparison between SEQ ID No. 19 and Genbank No. L08062, printed May 17, 2000.
Sequence Comparison between SEQ ID No. 20 and Genbank No. L08062, printed May 17, 2000.
Yap et al., *Database Genbank*, Database Accession No. AF116563 (Sep. 16, 1999), printed May 22, 2000.
Sequence Comparison between Genbank No. X68426 and Genbak No. AF116563, printed May 22, 2000.
Sequence Comparison between SEQ ID No. 15 and Genbank No. AF116563, printed May 22, 2000.
Sequence Comparison between SEQ ID No. 16 and Genbank No. AF116563, printed May 22, 2000.
Sequence Comparison between SEQ ID No. 107 and Genbank No. L08062, printed May 18, 2000.

* cited by examiner

METHOD AND NUCLEIC ACIDS FOR DETERMINING THE PRESENCE OF MICRO-ORGANISMS SPECIFIC TO THE BREWING PROCESS

The invention relates to a method for the detection of microorganisms relevant to brewing, as well as to nucleic acids and combinations thereof which can be used in this method. The invention further relates to the use of the nucleic acids according to the invention or combinations thereof for the detection and/or for the identification and/or characterisation of different genera or species of microorganisms relevant to brewing.

Beer can be regarded as very stable microbiologically, and can only be spoilt by a relatively manageable number of bacteria. In order to discover contamination with these organisms as early as possible, an analytical system which allows rapid detection of the microorganisms in the matrix beer must be used, since countermeasures must be undertaken immediately.

The common feature of all microorganisms harmful to beer is the trace contamination of individual vessels (barrels, bottles) and their slow growth. In particular, microbiological culturing of the anaerobic microorganisms is very difficult. The beer-spoiling bacteria at present known are classed into the following genera: Lactobacillus, Pediococcus, Pectinatus and Megasphaera. Members of the Selenomonas and Zymophilus genera have not yet emerged as beer contaminants; however, contamination of beer and their subsequent growth in it cannot be ruled out.

The genus Lactobacillus describes Gram positive, non-sporulating, mostly immotile and chain-forming rods, which are long, thin and sometimes curved. Coccoid forms are also sometimes observed. Members of the genus Lactobacillus are microaerophilic, and some are anaerobic. They are cytochrome- and catalase-negative, their metabolism is fermentative and they require a complex nutrient medium. The molar G+C content of the DNA is between 32 and 53%.

As well as in beer, Lactobacilli are found in dairy and cereal products, in meat and fish products, in water, waste water, wine, fruit and fruit juices, acid-pickled vegetables, sauerkraut, silage and sourdough. Although they are a component of the normal oral, intestinal and vaginal flora of mammals, they are however seldom pathogenic (Bergeys Manual of Syst. Microbiology, 1984, p. 1209–1234). In beer, because of their metabolic products, they lead to clouding and undesired flavour changes. Species relevant to beer spoilage are Lactobacillus brevis, Lactobacillus lindneri, Lactobacillus casei, Lactobacillus paracasei, Lactobacillus coryniformis and Lactobacillus curvatus (Back, Brauwelt, 1980, 120, p. 1562–1569).

The genus Pediococcus includes Gram positive, immotile and non-sporulating cocci. They form tetrads or occur as pairs. They are facultative anaerobes, and their oxygen sensitivity differs from species to species. Pediococci are cytochrome and catalase-negative and require a complex nutrient medium (Bergeys Manual of Syst. Microbiology, 1984, p. 1075–1079). They are used as starter cultures for the production of raw sausage products, they ferment various types of pickled vegetables and lead to the spoilage of foodstuffs (Firnhaber, Baumgart: Mikrobiologische Untersuchung von Lebensmitteln, 1993, p. 413–419, 115–117). The genus includes 8 species, and the species Pediococcus damnosus and Pediococcus inopinatus should be regarded as harmful to beer.

The genus Pectinatus includes the species Pectinatus cerevisiiphilus, Pectinatus frisingiensis and the strain Pectinatus sp. DSM 20764, not further taxonomically classified. All strains have been isolated from spoilt beer (Schleifer et al., Int. J. of Syst. Bacteriology, 1990, p. 19–27). These are slightly bent, non-sporulating rod-shaped bacteria. They have comb-like flagella, and are motile. They produce neither catalase nor cytochrome oxidase, and are obligate anaerobes. The molar G+C content is 38–41%. In the genus Pectinatus, and also in the genera Megasphaera, Selenomonas and Zymophilus, the cell wall is more similar to the Gram-positive bacteria than to the Gram-negative bacteria. Although the Gram staining is negative, they are taxonomically classified among the Gram-positive bacteria (Haikara, The Prokaryotes, $2^{nd}$ Edition, Vol. II, 1991, p. 1993–2004).

The genus Megasphaera includes the species Megasphaera elsdenii and Megasphaera cerevisiae. Only Megasphaera cerevisiae is relevant to brewing, and is described as a Gram negative, strictly anaerobic, cytochrome- and catalase-negative, immotile and sometimes slightly stretched coccus, which occurs singly, in pairs or in short chains. The mean cell diameter is about 1.4 μm, and the molar G+C content 42.4–44.8%. Main metabolites are sulphur compounds, such as $H_2S$ and volatile fatty acids. In beer, contamination with Megasphaera cerevisiae leads to very marked changes in aroma and taste (Haikara, The Prokaryotes, $2^{nd}$ Edition, Vol. II, 1991, p. 1993–2004).

Species of the genus Selenomonas are defined as obligate anaerobes, Gram negative, non-sporulating, slightly curved and motile rods. The molar G+C content is about 48–58% (Schleifer et al., Int. J. of Syst. Bacteriology, 1990, p. 19–27). Selenomonads are isolated from the stomach and intestinal tract and the dung of mammals. The genus includes 10 species (Hespell et al., The Prokaryotes, $2^{nd}$ Edition, Vol. II, 1991, p. 2005–2013). Only Selenomonas lacticifex has been isolated from starter yeast, and is thus relevant to brewing. Selenomonas lacticifex has not yet emerged as a beer-spoiling bacterium; however, its growth in beer is possible, and hence it fulfils the definition of a beer-spoiling organism.

The species Zymophilus paucivorans and raffinosivorans belong to the genus Zymophilus as Gram-negative, slightly bent, motile rods, which occur singly, in pairs or in short chains. The molar G+C content is about 38–41%. They are obligate anaerobes and have a fermentative metabolism. Both species are isolated from starter yeasts and brewery wastes; growth in beer has only been observed with Zymophilus raffinosivorans (Schleifer et al., Int. J. of Syst. Bacteriology, 1990, p. 19–27).

On the basis of comparison of the 16S rRNA gene sequences, all the genera to be tested are classified among the Gram-positive bacteria with low G+C content. The genera Pediococcus and Lactobacillus are classified into the Lactobacillaceae family, and the genera Pectinatus, Megasphaera, Selenomonas and Zymophilus into the Sporomusa group. The Sporomusa group is also described as a group of the Gram-positive Eubacteriales with Gram-negative cell wall (Stackebrandt et al., The Prokaryotes, $2^{nd}$ Edition, Vol. II, 1991, p. 25–26, 33).

A classical microbiological determination of the microorganisms described above can require up to 10 days. However, a markedly faster analysis is desirable, as otherwise unnecessary storage costs arise or the beer being tested has already been delivered. For these reasons, several rapid detection methods have already been developed. Thus, for example, organisms harmful to beer can be detected on the basis of their metabolic products (Haikara et al. Microbiology, 1995, 141, p. 1131–1137). Other indirect methods are turbidometry (Haikara et al., ASBC, 1990, p. 92–95) and measurement of the ATP bioluminescence (Miller et al., *J. Inst. Brew.*, 1989, Vol. 95, p. 317–319). Detection by means of antibodies is also rapid and specific (Gares et al., *ASBC*, 1993, p. 158–163; Winnewisser et al., *Int. J. of Bacteriology*, 1995, 45, p. 403–405). With these methods, the disadvantage is that either non-specific parameters are tested or only one species or genus is detected in each case. Also, the equipment and staff cost is high. An overview of rapid methods for the detection of contaminants relevant to brewing is given by Dowhanick (*Cerevisia*, 1995, 20/4, p. 40–49).

The polymerase chain reaction (PCR; Mullis et al., see U.S. Pat. No. 4,683,195, U.S. Pat. No. 4,683,202 and U.S. Pat. No. 4,965,188) is a rapid and effective method of specifically detecting organisms. A range of nucleic acids are known, through the use of which as primers and/or probes the specific detection of microorganisms relevant to brewing is possible. However, a disadvantage is that with the use of these nucleic acid molecules in an amplification or detection reaction, it is always only possible to detect a fraction of all possible microorganisms relevant to brewing. These PCR systems serve for the specific detection in each case only of individual species in an amplification reaction of the genera *Lactobacillus, Pediococcus, Pectinatus* and *Mega-sphaera* (Sakamoto U.S. Pat. No. 5,869,642; Nietupski et al., U.S. Pat. No. 5,705,339 and U.S. Pat. No. 5,484,900; Tsuchia et al., JP 06141899A, JP 06113888A/*ASBC J.*, 1992, p. 64–67/ *ASBC J.*, 1993, p. 40–41; Yasui JP07289295A/*Can. J. Microbiol.*, 1997, 43, p. 157–163, Shimada et al., JP06090793; Alatossava et al. WO97/09448; Doyle et al., *J. of Ind. Microbiology*, 1995, 15, p. 67–70; DiMichele et al., *ASBC J.*, 1993, p. 63–66; Vogeser et al, *Brauwelt*, 1998, 24/25, p. 1060–1063). Further, the methods described for visualisation of the amplification products, such as, for example, agarose gel electrophoresis, present problems, as the carcinogenic and highly toxic ethidium bromide is used for staining the amplification products. These methods can only be automated with difficulty and the assessment of the agarose gels or the identification of the microorganisms on the basis of the length of the amplification products is sometimes not clear.

The problem to be solved by the present invention was, therefore, to provide a method and means which make possible a rapid test of beer and brewing raw materials for contamination with microorganisms, the test being required to detect the whole range of possible beer-contaminating microorganisms.

This problem is solved according to the invention by a process which comprises the following steps:
(a) bringing the sample into contact with a combination of at least two first nucleic acid molecules (primers), which hybridise with a region of a microbial nucleic acid conserved in microorganisms relevant to brewing;
(b) amplification of the microbial nucleic acid or a portion thereof to produce at least one amplification fragment;
(c) bringing the amplification fragments obtained in step (b) into contact with at least one second nucleic acid molecule (probe), which specifically hybridises with at least one amplification fragment that comprises a sequence of the microbial nucleic acid specific for all microorganisms relevant to brewing or for one or several families, genera or species of microorganisms relevant to brewing; and
(d) detection of at least one hybrid nucleic acid which consists of an amplification fragment and a second nucleic acid molecule introduced in step (c), and by a nucleic acid molecule selected from:
(i) a nucleic acid with a sequence according to SEQ ID NO 1–107 or a fragment thereof at least 10, preferably 15–30, nucleotides long;
(ii) a nucleic acid which specifically hybridises with a nucleic acid according to (i);
(iii) a nucleic acid which is at least 70%, preferably at least 90%, identical with a nucleic acid according to (i) or (ii), or
(iv) a nucleic acid which is complementary to a nucleic acid according to (i) to (iii).

In the sequences according to SEQ ID NO 1–107, nucleotides are abbreviated as follows: G=guanosine, A=adenosine, T=thymidine, C=cytidine, U=uracil, i=inosine. In accordance with IUPAC, mixtures are abbreviated as follows: R=G or A, Y=C or T, K=G or T, W=A or T, S=C or G, M=A or C, B=C, G or T, D=A, G or T, H=A, C or T, V=A, C or G, and N=A, C, G or T.

For the determination of identity (in the sense of complete agreement, corresponding to 100% identity) with nucleic acid sequences according to (iii), partial sequences of a larger polynucleotide are considered. These partial sequences include 10 nucleotides and are identical when all 10 building blocks are identical in the two sequences compared. The nucleotides thymidine and uridine are to be regarded as identical. All possible fragments of a larger polynucleotide can be regarded as partial sequences.

Here 90% identity is present, when in the two sequences to be compared 9 out of 10 or 18 out of 20 nucleotides in one section are identical.

As an example, let us consider two polynucleotides which comprise 20 nucleotides and differ in the $5^{th}$ element. In a sequence comparison, six 10-nucleotide ones are then found which are identical, and 5 which are not identical, as they differ in one element.

Otherwise, the identity can also be determined by degree, the unit being stated in percent. For determination of the degree of identity, partial sequences are also considered, which as a minimum include the length of the sequence actually used, e.g., as primer, or else 20 nucleotides.

As an example, polynucleotides A with a length of 100 nucleotides and B with a length of 200 nucleotides are compared. From polynucleotide B, a primer with a length of 14 nucleotides is derived. For the determination of the degree of identity, polynucleotide A is compared with the primer over its whole length. If the sequence of the primer occurs in polynucleotide A, but differs in one element, then there is a fragment with a degree of identity of 13/14→92.3%.

In the second example, the whole of the aforesaid polynucleotides A and B are compared. In this case, all possible comparison windows of a length of 20 nucleotides are applied, and the degree of identity determined for them. Thus, if nucleotides 50–69 of polynucleotide A and B are identical with the exception of nucleotide No. 55, then for these fragments a degree of identity of 19/20→95% is found.

The method according to the invention can be carried out more rapidly than the previous microbiological detection methods, and makes it possible to detect several, preferably all, microorganisms relevant to brewing potentially present in a sample, such as, for example, even *Lactobacillus* species or members of the genera *Selenomonas* or *Zymophilus* seldom arising as contaminants, for which hitherto no detection method existed. The detection is comprehensive and indicates all contamination risks in the brewery. By means of the method according to the invention, microorganisms relevant to brewing can be detected both in beer samples and also in raw material samples (barley malt, yeast, hops, water) or samples of intermediate products in beer production (e.g. mash, wort) even when the number of contaminating microorganisms is still low.

In this context, microorganisms relevant to brewing are understood primarily to mean bacteria and in particular the bacteria described above, *Lactobacillus brevis, Lactobacillus lindneri, Lactobacillus casei, Lactobacillus paracasei, Lactobacillus coryniformis, Lacto-bacillus curvatus, Pediococcus damnosus, Pediococcus inopinatus, Pectinatus cerevisii-philus, Pectinatus frisingiensis, Pectinatus* sp. DSM 20764, *Megasphaera cerevisiae, Selenomonas lacticifex, Zymophilus paucivorans* and *Zymophilus raffinosivorans*, and also all microorganisms to be found in beer, which, while they do not belong to the aforesaid species, can nonetheless multiply in beer, for example, rare members of the Lactobacillaceae family, such as *Lactobacillus malefermentans, Lactobacillus buchneri, Lactobacillus parabuchneri, Lactobacillus sanfrancisco, Lactobacillus delbrueckii, Leuconostoc mesenteroides, Pediococcus pentosaceus* and *Lactococcus lactis*.

The microorganisms detectable by the method according to the invention are, thus, not limited to the microorganisms hitherto described as beer contaminants. Rather, the use of the nucleic acid molecules and the method according to the invention offers the possibility of recognising the presence of other microorganisms relevant to brewing, which have not previously been described as beer contaminants. A positive result at the level of higher taxonomic units (e.g. orders, families, genera) combined with a negative result at the level of the lower taxonomic units known to be relevant to brewing (e.g. species, subspecies, strains) indicates a contamination with such a non-typical microorganism relevant to brewing.

In a first step of the method according to the invention, the sample to be tested is brought into contact with a combination of at least two first nucleic acid molecules (primers). These nucleic acid molecules hybridise with a region of a microbial nucleic acid which is conserved in microorganisms relevant to brewing. The hybridisation takes place through pairing of the primer with regions of the microbial nucleic acid which have an at least partly complementary base sequence. The term "conserved" characterises the evolutionary variability of nucleotide sequences for species of different taxonomic units. If corresponding sequence sections from at least two microorganisms relevant to brewing are compared, the sequence can be regarded as variable or as conserved. Comparison sequences which are at least 95% identical are described as conserved, and those which are less than 95% identical as variable. Thus, a region of a nucleic acid conserved in microorganisms relevant to brewing denotes a region which is at least 95% identical in all microorganisms relevant to brewing (as defined above).

In a preferred embodiment of the present invention, the conserved region occurs in a genome section which contains the bacterial 23S and 5S genes. This region includes the intergenic spacer between the genes for the 23S rRNA and the 5S rRNA and the bounding 23S and 5S rDNA genes, and includes both conserved sequence regions and also hypervariable (i.e., very organism-specific) sequence regions. Prokaryotic ribosomes as a rule contain three distinct nucleic acid components, which are generally known as 5S, 16S and 23S rRNA (ribosomal nucleic acid). The genetic information for these ribonucleic acids (rDNA) is typically arranged in the genome as a tandem. The typical organisation of such a unit is 16S-23S-5S, where the genes are connected to one another by short hypervariable intergenic regions, so-called spacers. The units are present several times in the genome, and the number of operons can vary from species to species. The high conservation of the DNA sequence in certain sections of the ribosomal DNA over the whole bacterial kingdom allows the design of non-specific oligonucleotides even without exact knowledge of the individual DNA sequences of the organisms to be investigated. The sequences according to SEQ ID NO 1–20 according to the invention (Table 1) are sequences of the 23S-5S intergenic spacer of microorganisms relevant to brewing, from which nucleic acid molecules for use in the method according to the invention can be derived.

The combination of at least two first nucleic acid molecules used in the first step of the method according to the invention is selected, such that they are usable as primers in an amplification reaction, i.e., one nucleic acid molecule hybridises onto a first conserved region of the first strand of the target DNA and the other nucleic acid onto a second conserved region of the DNA strand complementary to the first, wherein the desired target region of the DNA is included. Both nucleic acid molecules have a length of at least 10 bp, preferably 15–30 bp. In a preferred embodiment of the invention, a combination of at least two nucleic acid molecules according to this invention is used. In a particularly preferred embodiment of the invention, a combination is used which includes at least one nucleic acid molecule with a sequence according to one of the SEQ ID NO 40 to 47 (Table 2) and at least one nucleic acid molecule with a sequence according to SEQ ID NO 48–54 or SEQ ID NO 55–59 or SEQ ID NO 60–72 (Table 2).

In a second step of the method according to the invention, the microbial nucleic acid or a portion thereof is amplified, whereby at least one amplification fragment is produced. Amplification is understood to mean the raising of the concentration of a nucleic acid or a portion thereof present in a reaction mixture. Processes used for the amplification of nucleic acids are for example the PCR (U.S. Pat. No. 4,683,195, U.S. Pat. No. 4,683,202 and U.S. Pat. No. 4,965,188), the "self-sustained sequence replication" (EP 329,822), the "transcription-based amplification system" (EP 310,229) and the "β-RNA replicase system" (U.S. Pat. No. 4,956,858). In a preferred embodiment of the present invention, the amplification comprises a polymerase chain reaction (PCR). In a further embodiment of the present invention, the amplification comprises a ligase-chain reaction or an isothermal nucleic acid amplification.

In a third step of the method according to the present invention, the amplification fragments obtained are brought into contact with at least one second nucleic acid molecule (probe). This nucleic acid molecule or these nucleic acid molecules hybridise specifically with at least one amplification fragment that comprises a sequence of the microbial nucleic acid which is specific for all microorganisms relevant to brewing or for one or several families, genera or species of microorganisms relevant to brewing, i.e., only occurs in members of these families or genera or in these species.

The double-strand formation of two identical or similar nucleotide fragments (DNA, RNA, PNA) is described as hybridisation. The term specific hybridisation is used when a stable hybrid nucleic acid between the oligonucleotide and the corresponding target DNA of the oligonucleotide exists, but not to other DNA than the target DNA. For the purposes of this invention, the feature "sequence which specifically hybridises with a sequence according to (i)" refers to a sequence, which under stringent conditions, hybridises with the sequence according to (i). For example, the hybridisations can be carried out at 50° C. with a hybridisation solution consisting of 2.5×SSC, 2× Denhardts solution, 10 mM Tris, 1 mM EDTA pH 7.5. Suitable washing conditions are for example four times repeated 1-minute washings in 0.1×SSC to 1.0×SSC, 2× Denhardts, 10 mM Tris, 1 mM EDTA, pH 7.5 at 20–50° C.

In a preferred embodiment of the invention, one or several of the nucleic acid molecules according to the invention is used as a second nucleic acid molecule (probe). Consensus probe is understood to mean a nucleic acid molecule which hybridises with highly conserved regions of a microbial nucleic acid and reacts with the amplification products of all microorganisms relevant to brewing. Nucleic acid molecules according to the invention which are usable as consensus probes have a sequence according to one of SEQ ID NO 40 to 72 (Table 2).

For the detection of a specific genus of microorganisms relevant to brewing, a nucleic acid molecule with a sequence according to one of SEQ ID NO 35 to 39 or SEQ ID NO 104 to 107 (Table 2) is preferably used. The genus specificity of a probe is defined as the ability of this probe to hybridise with the DNA of all isolates of as large as possible a group of members of the particular genus to be detected.

Species-specific nucleic acid probes are understood to mean nucleic acid molecules which hybridise with the DNA of all isolates of the particular species to be detected under the same stringency conditions. Species-specific nucleic acid molecules according to the invention with SEQ ID NO 21–22, SEQ ID NO 25–34, SEQ ID NO 73–78, SEQ ID NO 80–85 or SEQ ID NO 87–97 (Table 2) can be used.

The probes SEQ ID NO 23–24, SEQ ID NO 79, SEQ ID NO 86 and SEQ ID NO 98 to 103 are special cases. With the probes according to SEQ ID NO 23 and SEQ ID NO 79, strains of *Lactobacillus casei* and *Lactobacillus paracasei* ssp. *paracasei* can be detected. A probe according to SEQ ID NO 24 allows the detection of two subspecies of *Lactobacillus coryniformis* (*L. coryniformis* ssp. *coryniformis* and *L. coryniformis* ssp. *torquens*). With the probe SEQ ID NO 86, strains of the species *Pediococcus damnosus*, *Pediococcus inopinatus* and *Pediococcus parvulus* can be detected. With the use of these probes, other microorganisms relevant to brewing are not detected. Likewise, with the probes SEQ ID NO 98 to 103, all species of the Lactobacillaceae family relevant to brewing to be detected are detected, and other species and genera relevant to brewing are discriminated against.

In the last step of the method according to the invention, the detection of at least one hybrid nucleic acid which consists of an amplification fragment and a second nucleic acid molecule introduced in the preceding step takes place.

Preferably, first nucleic acid molecules (primers) and/or second nucleic acid molecules (probes) are at least 10 nucleotides, preferably 15–30 nucleotides long. In one embodiment of the present invention, the first and/or the second nucleic acid molecules are modified in that up to 20% of the nucleotides in 10 consecutive nucleotides, in particular 1 or 2 nucleotides of a block of 10 are replaced by nucleotides which do not occur naturally in bacteria.

The method according to the invention preferably includes the so-called consensus PCR. In this method, multiplication of the microbial nucleic acid or a portion thereof, and subsequent detection of these molecules by hybridisation with labelled specific probes take place. In the consensus PCR, nucleic acid molecules are used which make it possible to obtain an amplification product from several or, indeed, all of the relevant strains, subspecies, species or genera. The amplification does not lead to a differentiation of the microorganisms. The specificity of the detection is achieved through the subsequent hybridisation reaction with specific probes. In this way, microorganisms relevant to brewing can be simultaneously detected in a simple combination of amplification and detection reaction.

This kind of amplification and detection makes it possible to automate the detection reaction, so that a high sample throughput becomes possible. For example, a PCR-ELISA detection procedure can be used, in which the respective probes are bound in different wells of a microtitre plate, in which the hybridisation and the detection of the labelled amplification products then occurs. The detection can also be effected by the use of a microarray, on which several probes are immobilised, as a result of which the detection reaction can be carried out quickly and at no great cost.

In a preferred embodiment of the invention, the second nucleic acid molecule (probe) is modified or labelled in such a way that it can produce a detectable signal. The modification or labelling is selected from (i) radioactive groups, (ii) coloured groups, (iii) fluorescent groups, (iv) groups for immobilisation on a solid phase and (v) groups which permit an indirect or direct reaction, especially with the aid of antibodies, antigens, enzymes and/or substrates with affinity to enzymes or enzyme complexes.

For the purposes of this invention, labelling indicates directly or indirectly detectable groups or groups for immobilisation on a solid phase, which are attached to the nucleic acid molecule. Directly detectable are metal atoms, radioactive, coloured or fluorescent groups. Indirectly detectable are immunologically or enzymatically detectable groups, for example, antigens and antibodies, haptens or enzymes or enzymatically active parts of enzymes. These indirect groups are detected in subsequent reactions. Preferred are haptens which are coupled to an oligonucleotide and which are detected in a subsequent antibody reaction.

The nucleic acid molecules according to the invention can be used for the detection and/or for the identification and/or characterisation of bacteria relevant to brewing. The primers and/or probes described herein can also be used in the detection of the described microorganisms in drinks other than beer, in other samples from the brewing sector, such as for example in raw materials, starter yeast, environmental samples, in other foodstuff samples or in clinical samples, etc.

EXAMPLES

Example 1

Determination of the DNA Target Sequence of the Bacteria Harmful to Beer and Closely Related Species By sequence comparison of known 23S rDNA and 5S rDNA sequences (GenBank Sequence Database of the National Center of Biotechnology Information: NCBI), conserved gene regions were identified, which serve as hybridisation sites for the primers used for the sequencing. From pure cultures of the bacteria listed in Table 1, genomic DNA was isolated by known standard methods. With primers which hybridise in highly conserved regions, amplification products of all bacteria to be detected were obtained in a PCR. The following primers were used for the amplification and the subsequent sequencing:

Primer 1=SEQ ID NO 47:

5'-AAG TGC TGA AAG CAT CTA AG-3'

Primer 2=SEQ ID NO 55:

5'-GGC RRY GTC TAY TYT CSC-3'

| Composition of the PCR: | | |
| --- | --- | --- |
| Genomic DNA (10–100 ng) | 1.00 µl | |
| H₂O | 16.85 µl | |
| Buffer (10×) | 2.50 µl | 1× |
| dNTP (10 mM) | 0.50 µl | 200 µM |
| Primer 1 = Seq ID NO 48 (5 µM) | 1.50 µl | 0.30 µM |
| Primer 2 = Seq ID NO 49 (5 µM) | 1.50 µl | 0.30 µM |
| MgCl₂ (50 mM) | 1.00 µl | 2.00 mM |
| Taq-polymerase (5 U/µl) | 0.15 µl | 0.03 U/µl |
| Σ | 25.00 µl | |

| Temperature profile: | | |
| --- | --- | --- |
| 5 mins | 95° C. | |
| 30 secs | 95° C. | |
| 30 secs | 50° C. | ×38 |
| 30 secs | 72° C. | |
| 5 mins | 72° C. | |

These amplification products were purified via an agarose gel and by a subsequent treatment with the QIAquick PCR Gel Extraction Kit (Quiagen Co.) and sequenced in the Long Read Sequencer Model 4000L (LI-COR Co.) with the aforesaid primers, which are provided with an IRD-800 label. The resulting sequences of the 23S/5S rDNA spacer regions of the bacteria relevant to brewing and the phylogenetically closely related species were compared with one another and sequence regions identified which:

1.) are to be found in all species of the particular genus to be detected and at the same time differ from those of other genera or species,
2.) are only to be found in the particular species to be detected, but differ from other bacteria to be detected and not to be detected.

In the sequence regions described under 1.), hybridisation sites of genus-specific oligonucleo-tides were defined, and in the sequence regions described under 2.), the binding sites of species-specific oligonucleotides were defined.

Example 2

Detection of Bacteria Harmful to Beer by the Polymerase Chain Reaction

I. Amplification

Genomic DNA was isolated from pure cultures of the bacteria listed in Table 1 by known standard methods. Decimal dilutions from 1 fg/µl to 1 pg/µl of these preparations were then used in a PCR with the following composition:

Primer 3=SEQ ID NO 46:

5'-AAG GGC CAT CRC TCA ACG G-3'

Primer 4=SEQ ID NO 48:

5'-TGT GTT CGi iAT GGG AAC AGG TG-3'

| | | | |
| --- | --- | --- | --- |
| Genomic DNA | 1.00 µl | 4.00 µl | |
| H₂O | 16.60 µl | 66.40 µl | |
| Buffer (10×) | 2.50 µl | 10.00 µl | 1× |
| dNTP (10 mM) | 0.50 µl | 2.00 µl | 0.20 mM |
| Primer 3 = Seq ID NO 21 (5 µM) | 1.50 µl | 6.00 µl | 0.30 mM |
| Primer 4 = Seq ID NO 22 (5 µM) digoxigenin labelled | 1.50 µl | 6.00 µl | 0.30 mM |
| DMSO (100%) | 0.25 µl | 1.00 µl | 1.00% |
| MgCl₂ (50 mM) | 1.00 µl | 4.00 µl | 2.00 mM |
| Taq-polymerase (5 U/µl) | 0.15 µl | 0.60 µl | 0.03 U/µl |
| Σ | 25.00 µl | 100.00 µl | |

The PCR was performed under the following conditions in the Mastercycler® (Eppendorf Co.) according to the following temperature profile:

| | | |
| --- | --- | --- |
| 5 mins | 95° C. | |
| 30 secs | 95° C. | |
| 45 secs | 55° C. | ×38 |
| 90 secs | 72° C. | |
| 5 mins | 72° C. | |

Primer 3 (SEQ ID NO 46) was determined by sequence comparison of known 23S rDNA sequences (GenBank Sequence Database of NCBI). It hybridises onto highly conserved sequence sections in the 23S rDNA gene region. The binding site lies outside the region sequenced with the primers SEQ ID NO 48 and 49.

Primer 4 (SEQ ID NO 48) was determined on the basis of our own sequence data. The hybridisation site of primer 2 lies adjacent to the intergenic 23S/5S spacer in the 5S rDNA region.

II. Detection by PCR-ELISA

The detection is effected by PCR-ELISA. For this, per probe used, 5 µl of amplification product are treated with 5 µl of denaturation buffer (125 mM NaOH, 20 mM EDTA, pH 14) and incubated for 15 mins at room temperature. Each time, 2 pmoles of the particular biotinylated probe are pipetted into 100 µl of hybridisation buffer (2.5×SSC, 2× Denhardts solution, 10 mM Tris, 1 mM EDTA, pH 7.5) and transferred to the wells of a microtitre plate coated with streptavidin and preincubated at the hybridisation temperature of 50° C. After the denaturation, the denaturation mixture is pipetted into the hybridisation mixture. Next the mixture is incubated for 30 minutes at hybridisation temperature. If the hybridisation is complete, the hybridisation mixture is removed and the plate washed 4× with 200 µl of wash buffer 1 (WB1: 0.1×SSC, 2× Denhardts, 10 mM Tris, 1 mM EDTA, pH 7.6) for 1 min. each time at hybridisation temperature. Next, 100 µl of a solution of a horseradish peroxidase conjugated anti-digoxigenin antibody diluted according to the manufacturer's instructions is added (Boehringer Mannheim). The conjugate is diluted in wash buffer 2 (WB2: 100 mM Tris, 150 mM NaCl, 0.05% Tween 20, 0.5% blocking reagent, 100 µg/ml herring sperm, pH 7.6). Next, the antibody incubation is performed at 37° C. for 30 mins. After this, the plate is washed four times with 2001 µl of WB2 (at room temperature). After the washing, 100 µl of POD substrate (Boehringer Mannheim) are added and the mixture incubated for 20 mins at RT. Next the colour reaction is stopped with 100 µl of 0.5M H₂SO₄ and estimated at 450 nm.

III. Assessment

According to the detection protocol described above, the detection was performed for all bacteria and bacteria groups investigated, using the corresponding genus- and species-specific probes. Genus-specific probes are SEQ ID NO 35 for *Pediococcus*, SEQ ID NO 36 for *Pectinatus*, SEQ ID NO 37 for *Megasphaera*, SEQ ID NO 38 for *Selenomonas* and SEQ ID NO 39 for *Zymophilus*. Species-specific probes are SEQ ID NO 21 for *Lactobacillus brevis*, SEQ ID NO 22 for *Lactobacillus lindneri*, SEQ ID NO 23 for *Lactobacillus casei+paracasei*, SEQ ID NO 24 for *Lactobacillus coryniformis*, SEQ ID NO 25 for *Lactobacillus curvatus*, SEQ ID NO 26 for *Pediococcus damnosus*, SEQ ID NO 27 for *Pediococcus inopinatus*, SEQ ID NO 28 for *Pectinatus cervisiiphilus*, SEQ ID NO 29 for *Pectinatus frisingiensis*, SEQ ID NO 30 for *Pectinatus* sp. DSM20764, SEQ ID NO 31 for *Megasphaera cerevisiae*, SEQ ID NO 32 for *Selenomonas lacticifex*, SEQ ID NO 33 for *Zymophilus paucivorans* and SEQ ID NO 34 for *Zymophilus raffinosivorans*.

As controls, the consensus probes SEQ ID NO 40 and 41 were used, which hybridise with the amplification products of all the species to be detected. Further possible binding sites for consensus probes are SEQ ID NO 42–45. The probes of SEQ ID NO 40 to 45 were determined by sequence comparison of known 23S rDNA and 5S rDNA sequences (GenBank Sequence Database, NCBI).

If the extinction measured for a 1 fg quantity of genomic DNA used in the PCR was greater than 1, the result was assessed as positive. The results of the PCR-ELISA are presented in Table 3.

TABLE 1

| SEQ ID NO | Source Genus | Species | Strain | Description | Sequence |
|---|---|---|---|---|---|
| 1 | Lactobacillus | brevis | DSM 20054 | 23S-spacer-5S | 5'-TATATGGAAG TAAGACCCCT GAGAGATGAT CAGGTAGATA GGCTGGAAGT 50 AGCAGCGCCG TGAGGCGTGG AGCGGACCAG TACTAATCGG TCGAGGACTT 100 AACCAAGTCA ACAACGTAGT TGTTTCGAGA ATAATTGAAT AATATCTAGT 150 TTTGAGGGAA GAAGTTCTCT TATAGTGTGG TGGCGATAGC CTGAAGGATA 200 CACCTGTTCC CATGCCGAAC ACAGAAGTTA AGCTTCAGCA CGCCGATAGT 250 AGTTGGGGGA TCGCCCC-3' |
| 2 | Lactobacillus | lindneri | DSM 20690 | 23S-spacer-5S | 5'-CCATTCCTAT ATGGAAGTAA GACTCCTGAA AGATGATCAG GTCGATAGGT 50 TAGAAGTGGA AGCATAGTGA TATGTGAAGC GGACTAATAC TAATCAGTCG 100 AGGACTTAAC CAAGGAAGAC ACAGGGTTAA ATCAAAGTTG AACAGAGAAG 150 ATATTATCTA GTTTTGAGAG AACGAAGTTC GCTCAGGCTT ATGAAAAATA 200 AGCATAGTGT GGTGGCGATA GCCTGAAGGA TACACCTGTT CCCATGCCGA 250 ACACAGAAGT TAAGCTTCAG CACGCCAAAA GTAGTTGGGG GATCGCCCCC 300 TGCGAGGATA GGACGATGGT CATAGC-3' |
| 3 | Lactobacillus | casei | DSM 20011 | 23S-spacer-5S | 5'-CCATTCCTAT ATGGAAGTAA GACCCCTGAG AGATGATCAG GTAGATAGGC 50 TGGAAGTGGA AGTGCAGCGA TGCATGGAGC GGACCAGTAC TAATCGGTCG 100 AGGACTTAAC CAAGTAGAGC GTGAGCAGGA GCGCTTAGAA ACCGGAGCAT 150 AAGCGGGCCT GAGTTCGTTG GCCGGGTTTT GGCCAATGGA TTCAGGGTTC 200 TTATGTGGAG GTTTCTGCGA CTGCGAACGC GTTTCGATGA AATACACTGG 250 TTCCCGACAA CACAAAAACA ACAATGATAG CCAGTTTTGA GAGCGCAAAG 300 TTCTCATAAG TGTGGTGGCG ATAGCAAGAA GGATACACCT GTTCCCATGC 350 C-3' |
| 4 | Lactobacillus | paracasei ssp. paracasei | DSM 20008 | 23S-spacer-5S operon 1 | 5'-CCATTCCTAT ATGGAAGTAA GACCCCTGAG AGATGATCAG GTAGATAGGC 50 TGGAAGTGGA AGTGCAGCGA TGCATGGAGC GGACCAGTAC TAATCGGTCG 100 AGGACTTAAC CAAGTAAGAG TGTGAGCAGG AGCGGTTAGA AACCGGAGCA 150 TAAGCGGGCC TGAGCGTGAT GGCCGGGCTT TGGCCATTGC GGTCAGGGTC 200 CTTATGTGCA GGTTTCTGCG ACTGCGAACA CGTTTCGATG ACAAGTACGT 250 TAAGTTCAAG GCAGCAATTA AACAATGATA GCTAGTTTTG AGAGCGCAAA 300 GTTCTCATAA GTGTGGTGGC GATAGCAAGA AGGATACACC TGTTCCCATG 350 CCGAACACAG AAGTTAAGCT TCTTCACGCC GAGAGTAGTT GGTGGGAAAC 400 TGCCTGCGAG GATA-3' |
| 5 | Lactobacillus | paracasei ssp. paracasei | DSM 20008 | 23S-spacer-5S operon 2 | 5'-CCATTCCTAT ATGGAAGTAA GACCCCTGAG AGATGATCAG GTAGATAGGC 50 TGGAAGTGGA AGTGCAGCGA TGCATGGAGC GGACCAGTAC TAATCGGTCG 100 AGGACTTAAC CAAGTAAGCG TGCAAGCAGG AGCAGGTTTC TGCGACTGCG 150 AACACATTTC GATGACAAGT ACGTTAAGTT CAAGGCAGCA ATTAAACGAT 200 GATAGCCAGT TTTGAGACG CAAAGTTCTC ATAAGTGTGG TGGCGATAGC 250 AAGAAGGATA CACCTGTTCC CATGCCGAAC ACAGAAGTTA AGCTTCTTCA 300 CGCCGAGAGT AGTTGGTGGG AAACTGCCTG CGAGGATA-3' |
| 6 | Lactobacillus | coryniformis ssp. coryniformis | DSM 20001 | 23S-spacer-5S | 5'-CTCGAGTTGA GATTTCCCAT TCCTTTATGG AAGTAAGACC CCTGAGAGAT 50 GATCAGGTAG ATAGGTTGGA AGTGGACGTG CCGTGAGGCA TGGAGCGGAC 100 CAATACTAAT CGGTCGAGGA CTTAACCAAG TAGCATGTAC GTAGTGTTAG 150 TTTAAGGGCA AAGAAATGAA TATCCAGTTT TGAGAGCGCA ACGTTCTCAG 200 AAAGTGGTGT GGTGGCGATA GCAAGAAGGA TACACCTGTT CCCATGTCGA 250 ACACAGAAGT TAAGCTTCTT AGCGCCGAGA GTAGTTGGGG GAGCACCCCC 300 TGCGAGGATA GGACGAT-3' |
| 7 | Lactobacillus | coryniformis ssp. torquens | DSM 20004 | 23S-spacer-5S | 5'-CTCGAGATGA GATTTCCCAT TCCTTTATGG AAGTAAGACC CCTGAGAGAT 50 GATCAGGTAG ATAGGTTGGA AGTGGACGTG CCGTGAGGCA TGGAGCGGAC 100 CAATACTAAT CGGTCGAGGA CTTAACCAAG TAGCATGTAC GTGGTGTTAG 150 TTTAAGGGCA AAGAAATGAA TATCCAGTTT TGAGAGCGCA ACGTTCTCAG 200 AAAGTGGTGT GGTGGCGATA GCAAGAAGGA TACACCTGTT CCCATGTCGA 250 ACACAGAAGT TAAGCTTCTT AGCGCCGAGA GTAGTTGGGG GAGCACCCCC 300 TGCGAGGATA GGACGAT-3' |

TABLE 1-continued

| SEQ ID NO | Source Genus | Species | Strain | Description | Sequence |
|---|---|---|---|---|---|
| 8 | Lactoba-cillus | curvatus | DSM 20019 | 23S-spacer-5S | 5'-ACGCCTCGAG ATGAGATTTC CCATTCCTTT ATGGAAGTAA GACCCCTGAA 50<br>AGATGATCAG GTAGATAGGC TAGGAGTGGA AGTACAGCGA TGTATGGAGC 100<br>GGACTAGTAC TAATCGGTCG AGGACTTAAC CAAAGGTGCA ATGTTAGGCT 150<br>TTTGAAATGA AATATTACTT ATTATGCAGT TTTGAGAGAA CGAAGTTCTT 200<br>CTCAGTGCGC AAGCACAAAA TAGTGTGGTG GCGATAGCAA GAAGGATACA 250<br>CCTGTTCCCA TGTCGAACAC AGAAGTTAAG CTTCTTAGCG CCGATAGTAG 300<br>TTGGTGGGAA ACTACCTGCG AGGATAGGAC GATGGT-3' |
| 9 | Pedio-coccus | damnosus | DSM 20331 | 23S-spacer-5S | 5'-GATGAGATTT CCCATTCCAT TTATGGAAGT AAGACCCCTG AGAGATGATC 50<br>AGGTAGATAG GTTGGGAGTG GAAGTGTAGT GATACATGGA GCGGACCAAT 100<br>ACTAATCGGT CGAGGACTTA ACCACAAAGT GGTGTTCTCA AGAGAAGGAT 150<br>TCGATATTAT TTAGTTTTGA GAGAATAAAT TTCTTTCACA CGAGCCGCGT 200<br>AAGTGGATCG GAGAAGTGTG GTGACGATAG TGAGAAGGAT ACACCTGTTC 250<br>CCATGTCGAA CACAGAAGTT AAGCTTCTTA ACGCCGAGAG TAGTTGGGGG 300<br>ATCGCTCCCT GCGAGGATAG GACGATGGTC AATAG-3' |
| 10 | Pedio-coccus | inopinatus | DSM 20285 | 23S-spacer-5S | 5'-AGATGAGATT TCCCATTCCA TTTATGGAAG TAAGACCCCT GAGAGATGAT 50<br>CAGGTAGATA GGTTGGGAGT GGAAGTGTAG TGATACATGG AGCGGACCAA 100<br>TACTAATCGG TCGAGGACTT AACCACAAAG TGGTGTTCTC AAAGAGAAGA 150<br>TTTCGATATT ATTTAGTTTT GAGAGAATAA ATTTCTTTCA CACGAGCCGC 200<br>GGAAGTGGAT CGGAGAAGTG TGGTGACGAT AGTGAGAAGG ATACACCTGT 250<br>TCCCATGTCC AACACAGAAG TTAAGCTTCT TAACGCCGAG AGTAGTTGGG 300<br>GGATCGCTCC CTGCGAGGAT AGGACG-3' |
| 11 | Pectina-tus | cerevisii-philus | DSM 20467 | 23S-spacer-5S | 5'-AAGTGCTGAA AGCATCTAAG CGTGAAACCT GCCTTAAGAT GAGGTTTCCC 50<br>AGAGCCGTAA GGCTTGGAAG GCACCTTGAA TAAGACGAGG TAGATAGGCC 100<br>GGAGTAGAA GTACAGTAAT GTACGAAGCG GACTGGTACT AATAAGCCGA 150<br>GAGCTTAACT TAAAATCATC GAAAAAAATG TTTGGTCTGA GATTTCTTCT 200<br>GTGAAGTTTT GAGTGTGCAA GACACTCTGG TTGAAGGGCA GGGAACGTGA 250<br>GAGCGTAAAA CTGCGGACTT TGGCTCAAAG AGTTAAAGCA TCTGGTGACG 300<br>ATACCTGGAT GGATCCACCT GTTCCCATTC CGAACACAGT AGTTAAGCAT 350<br>CCACAGGCTG AAGGTACTTG GGGGGCGACC CCCTGGGAAA ATAGGACACT 400<br>GCC-3' |
| 12 | Pectina-tus | frisingen-sis | DSM 6306 | 23S-spacer-5S | 5'-AAGTGCTGAA AGCATCTAAG CGTGAAACCA GCTTTAAGAT GAGGTTTCCC 50<br>AGAACGCAAG TTTTGAAGGC ACCTTGAAGA AGACGAGGTA GATAGGCCGG 100<br>GAGTGGAAGT ATGGTGACAT ATGAAGCGGA CTGGTACTAA TAAGCCGAGA 150<br>GCTTAACTTG ATTTCATCAA AAAAGAGAAA TGTTTGGTCA GAGATTTTCT 200<br>TCTGTGAAGT TTTGAGTGTG CAAGAACACT CGAGAGTATA TAGGTAAAGG 250<br>AAAAGCAGCA GATAAGTTTC CTGGTTACTG TATATACCGG CTGAGGTGCT 300<br>GAGGCACTGA AGGCCAGAAC ATCTGGTGGC GATACCTGGA TGGATCCACC 350<br>TGTTCCCATT CCGAACACAG TAGTTAAGCA TCCACAGGCC GAAGGTACTT 400<br>GGGGGGCAGC CCCCTGCGAA AATAGGACAC CGCC-3' 450 |
| 13 | Pectina-tus | sp. | DSM 20764 | 23S-spacer-5S operon 1 | 5'-AAGTGCTGAA AGCATCTAAG CGTGAAACCT GCCTTAAGAT GAGGTTTCCC 50<br>AGAGCCGTAA GGCTTGGAAG GCACCTTGAA GATGACGAGG TAGATAGGCC 100<br>GGGAGTAGAA GTATGGTGAC ATACGAAGCG GACTGGTACT AATAAGCCGA 150<br>GAGCTTAACT TAATTTCATC TATAAATGTT TGGTCCTGAT TTCTTCTGTG 200<br>AAGTTTTGAG TGTGCAAGAT CACTCATGAA GTATATAGGT AAAGGGAAA 250<br>GCAGCAGATT AGTTCCTGGT TTACTTTATA TATGAGCACT AAGGTGCAGA 300<br>AAAGAACGTT TGAGGAAACG CGGCGTTCGT AAACTCACTT TGCGTGCTGA 350<br>TTATCTCAAT GCTAAAGCAT TAAGATAATT TTAGAGGAAA CGCGCGTTCA 400<br>CTAGCGTTCA CTCTGCGTAC TTTATTTCTA AGTGCTGAAG CACTAAGAAG 450<br>GGCAAGGAAA CGCGTCGTTC GCGATGCTCA CTTTGCGTAC TTCATCTCTA 500<br>GACTGCTAAA GCAGTAAGAT CTGAAGCATC TGGTGGCGAT ACCTGGATGG 550<br>ATCCACCTGT TCCCATTCCG AACACAGTAG TTAAGCATCC ACAGGCCGAA 600<br>GGTACTTGGG GGCAGCCCC CTGCGAGAGT AGGACATCGC C-3' |
| 14 | Pectina-tus | sp. | DSM 20764 | 23S-spacer-5S operon 2 | 5'-AAGTGCTGAA AGCATCTAAG CGTGAAACCT GCCTTAAGAT GAGGTTTCCC 50<br>AGAGCCGTAA GGCTTGGAAG GCACCTTGAA GATGACGAGG TAGATAGGCC 100<br>GGGAGTAGAA GTATGGTGAC ATACGAAGCG GACTGGTACT AATAAGCCGA 150<br>GAGCTTAACT TAATTTCATC TATAAATGTT TGGTCCTGAT TTCTTCTGTG 200<br>AAGTTTTGAG TGTGCAAGAT CACTCATGAA GTATATAGGT AAAGGGGAA 250<br>GCAGATTAGT TCCTGGTTTA CTTTATATAT GAGCACTAAG GTGCAGAAAA 300<br>GAACGTCTAA GGAAACGCGG CGTTCGTAGG CTCACTCTGC GTACTTCATC 350<br>TCTAGACTGC TAAAGCAGTA AGATCTGAAG CATCTGGTGG CGATACCTGG 400<br>ATGGATCCAC CTGTTCCCAT TCCGAACACA GTAGTTAAGC ATCCACAGGC 450<br>CGAAGGTACT TGGGGGGCA CCCCCTGCGA AAGTAGGACA CCGCC-3' |
| 15 | Mega-sphaera | cerevisiae | DSM 20462 | 23S-spacer-5S operon 1 | 5'-GCATCTAAGC GTGAAACCAG CCTAGAGATG AGGTTTCTCA TTACGAAAGT 50<br>AAGTAAGGTC CCATGAAGAC GACATGGTAG ATAGGCCGGG AGTGGACGTA 100<br>CAGTAATGTA TGGAGCGGAC CGGTACTAAT AGACCGAGGA CTTGACTTAA 150<br>GCAGGGAACC CATTTTAAAG AAGCGAAGCG ACGCATAAAA TGGAGTGAGT 200<br>CGCTTATACC GAATCGCAGA TTCGGTAAAG CAGCGGAACA TACCAATGCA 250<br>GCGGCAACAC CAGTTAGCAT AAACTAAGCG GATTCGGAGT GGGTGAGGGA 300<br>GTTTCGTAGC AGCGTAGGCT AACCCAACCA CCGCTTTCGA AGAAGGCGAA 350<br>TGGTTTGAAA AAGAGTACAT GCGAAGAAAC GACGAAAGAC TCACAACCAA 400<br>AACATACAAA CTAAGTAGAT GACATTAGAG TCACACCGAT TGTTAAGATC 450<br>CGAAATACTT TTCGATGTAG TTGTCAGGAT ACGAATCCTG AAACGAATTC 500<br>AGTGGTGATG GCTGCAGGGA TCCACCTGTT CCCATACCGA ACACAG-3' |

TABLE 1-continued

| SEQ ID NO | Source Genus | Species | Strain | Description | Sequence |
|---|---|---|---|---|---|
| 16 | Mega-sphaera | cerevisiae | DSM 20462 | 23S-spacer-5S operon 2 | 5'-GCATCTAACC GTGAAACCAG CCTAGAGATG AGGTTTCTCA TTACGAAAGT 50<br>AAGTAAGGTC CCATGAAGAC GACATGGTAG ATAGGCCGGG AGTGGACGTA 100<br>CAGTAATGTA TGGAGCGGAC CGGTACTAAT AGACCGAGGA CTTGACTTAA 150<br>GCAAAGAAGC AATAGAAAGA ACCATGTAGA TGGTGTAAGA GTTAGACGGG 200<br>TAGTTAAGGT CCGAAATACT TTTCGATGTA GTTGTCAGGA TACGAATCCT 250<br>GAAACGAATT CAGTGGTGAT GGCTGCAGGG ACCACCTGTT CCCATACCGA 300<br>ACACAG-3' |
| 17 | Selenomo-nas | lacticifex | DSM 20757 | 23S-spacer-5S operon 1 | 5'-AAGTGCTGAA AGCATCTAGG CGTGAAGCCT GTCCCGAGAT GAAGTATCTC 50<br>ATGGAGTAAT CCAGTGAAGT TCCTTGAAGA AGACAAGGTA GATAGGTTGG 100<br>GAGTGTAAGC ATCGTAAGGT GTTCAGCGGA CCAATACTAA TAAATCGAGG 150<br>GCTTAACTTT ACAGACCTGT CCAAGAAGCG AAGCGGATTG GGTAACAGGT 200<br>CGTATGCGAA AACATCCCAA GAATCGAGTC CGAAGGGCGA AGATGATTGG 250<br>CAGATGTTGA CCGCTAATAA TCTAGAATGT TTCGATACAA TTTTTCTTCT 300<br>GTATAGTTTT GAGTGGACAT CGTTCATTCA ATAATATCCA GTGACGATAG 350<br>CTGAGTGGTA CCACCTGTTC CCATACCGAA CACAGTAGTT AAGCACTCAT 400<br>ACGCCGAAAG TACTTGTCTG GAAACGGGCT GCGAGAATAG GACGTCGCC-3' |
| 18 | Selenomo-nas | lacticifex | DSM 20757 | 23S-spacer-5S operon 2 | 5'-AAGTGCTGAA AGCATCTAAG CGTGAAGCCT GTCCCGAGAT GAAGTATCTC 50<br>ATGGAGTAAT CCAGTGAAGT TCCTTGAAGA AGACAAGGTA GATAGGTTGG 100<br>GAGTGTAAGC ATCGTAAGGT GTTCAGCGGA CCAATACTAA TAAATCGAGG 150<br>GCTTATCTTA ATAATCTAGA ATGTTTCGAT ACAATTTTTC TTCTGTATAG 200<br>TTTTGAGTGG ACATGGTTCA TTCAATAATA TCCAGTGACG ATAGCTGAGT 250<br>GGTACCACCT GTTCCCATAC CGAACACAGT AGTTAAGCAC TCATACGCCG 300<br>AAAGTACTTG TCTGGAAACG GGCTGCGAAA ATAGGACGCC GCC-3' |
| 19 | Zymophil-us | raffino-sivorans | DSM 20765 | 23S-spacer-5S | 5'-AAGTGCTGAA AGCATCTAAG CGTGAAACCA GCCTTAAGAT GAGGTTTCTC 50<br>ACAGAGCAAT CTGGTAAGAC CCCTTGAAGA AGACAAGGTA GATAGGTCGG 100<br>GAGTGGAAGC GCAGTAATGT GTGCAGCGGA CCGATACTAA TAGGTCGAGG 150<br>GCTTGACTTA AAGCCAGAAC GAAAACTAAA ATGCGAACAT TTCTTTCTTC 200<br>TGTATAGTTT TGAGAGAACA AACTCTTAAG ATGGAGTAGT CTGAGGCGAA 250<br>AGCGGAAGGC AGCGATATCT AAAAAAAGAA TATCTGGTAG TGATAGCCAA 300<br>GTGGACCCAC CTGTTCCCAT ACCGAACACA GTAGTTAAGC ACTTGAACGT 350<br>CGAAAGTACT TGGGTGGAAA CGCCCTGCGA AAATAGGACA CCGCC-3' |
| 20 | Zymophil-us | paucivorans | DSM 20759 | 23S-spacer-5S | 5'-AAGTGCTGAA AGCATCTAAG CGTGAAACCA GCCTTAAGAT GAGGTTTCTC 50<br>ACAGAGCAAT CTGGTAAGAC CCCTTGAAGA AGACAAGGTA GATAGGTCGG 100<br>GAGTGGAAGC GCAGTAATGT GTGTAGCGGA CCGATACTAA TAGGTCGAGG 150<br>GCTTGACTTA AAGCCAGAAC GAATTCTAAA ATGCGAACAT TTCTTTCTTC 200<br>TGTATAGTTT TGAGAGAACA GACTCTTAAG ATGAGCAGTC TGAGGCGAAA 250<br>GCTAAAGGCA GCGATATCTA AAAAAAGAA TATCTGGTAG TGATAGCCAA 300<br>GTGGACCCAC CTGTTCCCAT ACCGAACACA GTAGTTAAGC ACTTGAACGT 350<br>CGAAAGTACT TGGGTGGAAA CGCCCTGGGA AAATAGGACA CCGCC-3' |

TABLE 2

| SEQ ID NO | Description | | Sequence | |
|---|---|---|---|---|
| 21 | Lactobacillus brevis | Specific probe | 5'- CCAAGTCAACAACGTAGTTGT | -3' |
| 22 | Lactobacillus lindneri | Specific probe | 5'- GACACAGGGTTAAATCAAAGTTG | -3' |
| 23 | Lactobacillus casei<br>Lactobacillus paracasei ssp. paracasei | Specific probe | 5'- AGGTTTCTGCGACTGCGAAC | -3' |
| 24 | Lactobacillus coryniformis ssp. coryniformis<br>Lactobacillus coryniformis ssp. torquens | Specific probe | 5'- ATGTACGTAGTGTTAGTTTAAGGGC | -3' |
| 25 | Lactobacillus curvatus | Specific probe | 5'- CTTCTCAGTGCGCAAGCACA | -3' |
| 26 | Pediococcus damnosus | Specific probe | 5'- GTGTTCTCAAGAGAAGGATTCG | -3' |
| 27 | Pediococcus inopinatus | Specific probe | 5'- GTTCTCAAAGAGAAGATTTCGATATTA | -3' |
| 28 | Pectinatus cerevisiiphilus | Specific probe | 5'- TGAGAGCGTAAAACTGCGGACTT | -3' |
| 29 | Pectinatus frisingensis | Specific probe | 5'- CAGATAAGTTTCCTGGTTACTG | -3' |
| 30 | Pectinatus sp. DSM 20764 | Specific probe | 5'- CACTAAGGTGCAGAAAAGAACGT | -3' |
| 31 | Megasphaera cerevisiae | Specific probe | 5'- CTTTTCGATGTAGTTGTCAGGATACG | -3' |
| 32 | Selenomonas lacticifex | Specific probe | 5'- GTTCATTCAATAATATCCAGTGACG | -3' |
| 33 | Zymophilus raffinosivorans | Specific probe | 5'- AACTCTTAAGATGGAGYAGTCTG | -3' |
| 34 | Zymophilus paucivorans | Specific probe | 5'- ACTCTTAAGATGAGcAGTCTGA | -3' |
| 35 | Pediococcus genus | genus-specific probe | 5'- AGTSTAGTGATACATGGAGCG | -3' |
| 36 | Pectinatus genus | genus-specific probe | 5'- GTGAAGTTTTGAGTGTGCAAGA | -3' |

TABLE 2-continued

| SEQ ID NO | Description | | Sequence | |
|---|---|---|---|---|
| 37 | *Megasphaera* genus | genus-specific probe | 5'- GACCGAGGACTTGACTTAAGCA | -3' |
| 38 | *Selenomonas* genus | genus-specific probe | 5'- TCCAGTGACGATAGCTGAGT | -3' |
| 39 | *Zymophilus* genus | genus-specific probe | 5'- AAGAATATCTGGTAGTGATAGCCAA | -3' |
| 40 | consensus sequence | | 5'- GTCGTGAGACAGTTCGGTC | -3' |
| 41 | consensus sequence | | 5'- CYTAGTACGAGAGGACCGGRR | -3' |
| 42 | consensus sequence | | 5'- GCTACCCTGGGGATAACAGGC | -3' |
| 43 | consensus sequence | | 5'- ATCGACGGGGAGGTTTSSCAC | -3' |
| 44 | consensus sequence | | 5'- CACCTCGATGTCGGCTCRTC | -3' |
| 45 | consensus sequence | | 5'- CCAAGGGTTGGGCTGTTC | -3' |
| 46 | consensus sequence | | 5'- AAGGGCCATCRCTCAACGG | -3' |
| 47 | consensus sequence | | 5'- AAGTGCTGAAAGCATCTAAG | -3' |
| 48 | consensus sequence | | 5'- TGTGTTCGiiATGGGAACAGGTG | -3' |
| 49 | consensus sequence | | 5'- TGTGTTCGGAATGGGAACAGGTG | -3' |
| 50 | consensus sequence | | 5'- TGTGTTCGAAATGGGAACAGGTG | -3' |
| 51 | consensus sequence | | 5'- TGTGTTCGGTATGGGAACAGGTG | -3' |
| 52 | consensus sequence | | 5'- TGTGTTCGATATGGGAACAGGTG | -3' |
| 53 | consensus sequence | | 5'- TGTGTTCGGCATGGGAACAGGTG | -3' |
| 54 | consensus sequence | | 5'- TGTGTTCGACATGGGAACAGGTG | -3' |
| 55 | consensus sequence | | 5'- GGCRRYGTCCTAYTYTCSC | -3' |
| 56 | consensus sequence | | 5'- GGCAGTGTCCTACTTTCCC | -3' |
| 57 | consensus sequence | | 5'- GGCAGCGTCCTACTTTCGC | -3' |
| 58 | consensus sequence | | 5'- GGCAGTGTCCTACTTTCGC | -3' |
| 59 | consensus sequence | | 5'- GGCAGCGTCCTACTTTCCC | -3' |
| 60 | consensus sequence | | 5'- GYTTMRCTTCYRDGTTCG | -3' |
| 61 | consensus sequence | | 5'- GCTTAACTTCCGTGTTCG | -3' |
| 62 | consensus sequence | | 5'- GCTTAACTTCTATGTTCG | -3' |
| 63 | consensus sequence | | 5'- GCTTAACTTCTGTGTTCG | -3' |
| 64 | consensus sequence | | 5'- GCTTAACTTCCATGTTCG | -3' |
| 65 | consensus sequence | | 5'- GCTTAACTTCCGGGTTCG | -3' |
| 66 | consensus sequence | | 5'- GCTTAACTTCTAGGTTCG | -3' |
| 67 | consensus sequence | | 5'- GCTTAACTTCTGGGTTCG | -3' |
| 68 | consensus sequence | | 5'- GCTTAACTTCCAGGTTCG | -3' |
| 69 | consensus sequence | | 5'- GCTTAACTTCCGAGTTCG | -3' |
| 70 | consensus sequence | | 5'- GCTTAACTTCTAAGTTCG | -3' |
| 71 | consensus sequence | | 5'- GCTTAACTTCTGAGTTCG | -3' |
| 72 | consensus sequence | | 5'- GCTTAACTTCCAAGTTCG | -3' |
| 73 | *Lactobacillus brevis* | specific probe | 5'- TCGAGAATAATTGAATAATATCTAG | -3' |
| 74 | *Lactobacillus brevis* | specific probe | 5'- GAGGGAAGAAGTTCTCTTAT | -3' |
| 75 | *Lactobacillus lindneri* | specific probe | 5'- AACAGAGAAGATATTATCTAGTT | -3' |
| 76 | *Lactobacillus lindneri* | specific probe | 5'- TTGAGAGAACGAAGTTCGCTCAGGCTTATGAAAAATAAGCAT | -3' |
| 77 | *Lactobacillus casei* | specific probe | 5'- TTCGTTGGCCGGGTTTTGGCCAATGGATTCAGGGTTCTTATGTGG | -3' |
| 78 | *Lactobacillus casei* | specific probe | 5'- GCGTTTCGATGAAATACACTGGTTCCCGACAACACAAAAACAACAATGA TAGCCAGTT | -3' |
| 79 | *Lactobacillus casei* *Lactobacillus paracasei* | specific probe | 5'- TTAGAAACCGGAGCATAAGCGGGCCTGAG | -3' |
| 80 | *Lactobacillus paracasei* | specific probe | 5'- GCGTGATGGCCGGGCTTTGGCCATTGCGGTCAGGGTCCTTATGTGC | -3' |
| 81 | *Lactobacillus paracasei* | specific probe | 5'- CAAGTACGTTAAGTTCAAGGCAGCAATTAAACAATGATAGCTAGTT | -3' |
| 82 | *Lactobacillus coryniformis* | specific probe | 5'- AAAGAAATGAATATCCAGTTTTGAGAGCGCAACGTTCTCAGAAA | -3' |
| 83 | *Lactobacillus curvatus* | specific probe | 5'- AGGTGCAATGTTAGGCTTTTGAAATGAAATATTACTTATTATGCAGTT | -3' |
| 84 | *Pediococcus damnosus* | specific probe | 5'- GCCGCGTAAGTGGATCGGAGAA | -3' |
| 85 | *Pediococcus inopinatus* | specific probe | 5'- GCCGGGAAGTGGATCGGAGAA | -3' |
| 86 | *Pediococcus damnosus* *Pediococcus inopinatus* *Pediococcus parvulus* | specific probe | 5'- GAGAGAATAAATTTCTTTCACACGA | -3' |
| 87 | *Pectinatus cerevisiiphilus* | specific probe | 5'- AAAATCATCGAAAAAAATGTTTGGTCTGAGATTTCTTCT | -3' |
| 88 | *Pectinatus cerevisiiphilus* | specific probe | 5'- CACTCTGGTTGAAGGGCAGGGAACG | -3' |
| 89 | *Pectinatus frisingensis* | specific probe | 5'- GATTTCATCAAAAAAGAAAATGTTTGGTCAGAGATTTT | -3' |
| 90 | *Pectinatus frisingensis* | specific probe | 5'- TATATACCGGCTGAGGTGCTGAGGCACTGAAGG | -3' |
| 91 | *Pectinatus* sp. DSM 20764 | specific probe | 5'- AATTTCATCTATAAATGTTTGGTCCTGATTTCTTCT | -3' |
| 92 | *Pectinatus* sp. DSM 20764 | specific probe | 5'- AGATTAGTTCCTGGTTTACTTTATATATGAGCACTAAGGTGCAGAAAAG AACGT | -3' |
| 93 | *Pectinatus* sp. DSM 20764 | specific probe | 5'- AGGAAACGCGGCGTTCGTAA | -3' |
| 94 | *Selenomonas lacticifex* | specific probe | 5'- TAATAATCTAGAATGTTTCGATACAATTTTTCTTCTGTATAGTTTTGAG TGGACAT | -3' |

TABLE 2-continued

| SEQ ID NO | Description | | Sequence | |
|---|---|---|---|---|
| 95 | Zymophilus raffinosivorans | specific probe 5'- | GAGGCGAAAGCGGAAGGCAGCGAT | -3' |
| 96 | Zymophilus paucivorans | specific probe 5'- | GAGGCGAAAGCTAAAGGCAGCGAT | -3' |
| 97 | Megasphaera cerevisiae | specific probe 5'- | AATCCTGAAACGAATTCAGTGGTGATGGCTGCAGGGA | -3' |
| 98 | Detection of all | 5'- | TATGGAAGTAAGACCCCTGA | -3' |
| 99 | Lactobacillaceae relevant to | brewing for 5'- | AGATGATCAGGTAGATAGGCT | -3' |
| 100 | differentiation from other | 5'- | AGATGATCAGGTCGATAGGTT | -3' |
| 101 | bacteria relevant to brewing | 5'- | AGATGATCAGGTAGATAGGTT | -3' |
| 102 | | 5'- | TACTAATCGGTCGAGGACTTAACCA | -3' |
| 103 | | 5'- | ATACTAATCAGTCGAGGACTTAACCA | -3' |
| 104 | Pectinatus genus | genus-specific probe 5'- | GAAGCGGACTGGTACTAATAAGCCGAGAGCTT | -3' |
| 105 | Selenomonas genus | genus-specific probe 5'- | CAGCGGACCAATACTAATAAATCGAGGGCTTA | -3' |
| 106 | Zymophilus genus | genus-specific probe 5'- | AGCGGACCGATACTAATAGGTCGAGGGCTTGACTTAAA | -3' |
| 107 | Megasphaera genus | genus-specific probe 5'- | GGAGCGGACCGGTACTAATAGACCGAGGACTT | -3' |

TABLE 3

| | SEQ ID NO 21 | SEQ ID NO 22 | SEQ ID NO 23 | SEQ ID NO 24 | SEQ ID NO 25 | SEQ ID NO 26 | SEQ ID NO 27 | SEQ ID NO 28 | SEQ ID NO 29 | SEQ ID NO 30 | SEQ ID NO 31 | SEQ ID NO 32 |
|---|---|---|---|---|---|---|---|---|---|---|---|---|
| Lactobacillus brevis | + | − | − | − | − | − | − | − | − | − | − | − |
| Lactobacillus lindneri | − | + | − | − | − | − | − | − | − | − | − | − |
| Lactobacillus casei | − | − | + | − | − | − | − | − | − | − | − | − |
| Lactobacillus paracasei paracasei | − | − | + | − | − | − | − | − | − | − | − | − |
| Lactobacillus coryniformis coryniformis | − | − | − | + | − | − | − | − | − | − | − | − |
| Lactobacillus coryniformis torquens | − | − | − | + | − | − | − | − | − | − | − | − |
| Lactobacillus curvatus | − | − | − | − | + | − | − | − | − | − | − | − |
| Pediococcus damnosus | − | − | − | − | − | + | − | − | − | − | − | − |
| Pediococcus inopinatus | − | − | − | − | − | − | + | − | − | − | − | − |
| Pectinatus cerevisiiphilus | − | − | − | − | − | − | − | + | − | − | − | − |
| Pectinatus frisingensis | − | − | − | − | − | − | − | − | + | − | − | − |
| Pectinatus sp. DSM 20462 | − | − | − | − | − | − | − | − | − | + | − | − |
| Megasphaera cerevisiae | − | − | − | − | − | − | − | − | − | − | + | − |
| Selenomonas lacticifex | − | − | − | − | − | − | − | − | − | − | − | + |
| Zymophilus raffinosivorans | − | − | − | − | − | − | − | − | − | − | − | − |
| Zymophilus paucivorans | − | − | − | − | − | − | − | − | − | − | − | − |

TABLE 3-continued

|  | SEQ ID NO 33 | SEQ ID NO 34 | SEQ ID NO 35 | SEQ ID NO 36 | SEQ ID NO 37 | SEQ ID NO 38 | SEQ ID NO 39 | SEQ ID NO 40–45 |
|---|---|---|---|---|---|---|---|---|
| *Lactobacillus brevis* | − | − | − | − | − | − | − | + |
| *Lactobacillus lindneri* | − | − | − | − | − | − | − | + |
| *Lactobacillus casei* | − | − | − | − | − | − | − | + |
| *Lactobacillus paracasei paracasei* | − | − | − | − | − | − | − | + |
| *Lactobacillus coryniformis coryniformis* | − | − | − | − | − | − | − | + |
| *Lactobacillus coryniformis torquens* | − | − | − | − | − | − | − | + |
| *Lactobacillus curvatus* | − | − | − | − | − | − | − | + |
| *Pediococcus damnosus* | − | − | + | − | − | − | − | + |
| *Pediococcus inopinatus* | − | − | + | − | − | − | − | + |
| *Pectinatus cerevisiiphilus* | − | − | − | + | − | − | − | + |
| *Pectinatus frisingensis* | − | − | − | + | − | − | − | + |
| *Pectinatus sp. DSM 20462* | − | − | − | + | − | − | − | + |
| *Megasphaera cerevisiae* | − | − | − | − | + | − | − | + |
| *Selenomonas lacticifex* | − | − | − | − | − | + | − | + |
| *Zymophilus raffinosivorans* | + | − | − | − | − | − | + | + |
| *Zymophilus paucivorans* | − | + | − | − | − | − | + | + |

SEQUENCE LISTING

<160> NUMBER OF SEQ ID NOS: 107

<210> SEQ ID NO 1
<211> LENGTH: 267
<212> TYPE: DNA
<213> ORGANISM: Lactobacillus brevis

<400> SEQUENCE: 1

```
tatatggaag taagacccct gagagatgat caggtagata ggctggaagt agcagcgccg      60
tgaggcgtgg agcggaccag tactaatcgg tcgaggactt aaccaagtca acaacgtagt     120
tgtttcgaga ataattgaat aatatctagt tttgagggaa gaagttctct tatagtgtgg     180
tggcgatagc ctgaaggata cacctgttcc catgccgaac acagaagtta agcttcagca     240
cgccgatagt agttggggga tcgcccc                                         267
```

<210> SEQ ID NO 2
<211> LENGTH: 326
<212> TYPE: DNA
<213> ORGANISM: Lactobacillus lindneri

<400> SEQUENCE: 2

```
ccattcctat atggaagtaa gactcctgaa agatgatcag gtcgataggt tagaagtgga      60
agcatagtga tatgtgaagc ggactaatac taatcagtcg aggacttaac caaggaagac     120
```

```
acagggttaa atcaaagttg aacagagaag atattatcta gttttgagag aacgaagttc    180
gctcaggctt atgaaaaata agcatagtgt ggtggcgata gcctgaagga tacacctgtt    240
cccatgccga acacagaagt taagcttcag cacgccaaaa gtagttgggg gatcgccccc    300
tgcgaggata ggacgatggt catagc                                         326
```

<210> SEQ ID NO 3
<211> LENGTH: 351
<212> TYPE: DNA
<213> ORGANISM: Lactobacillus casei

<400> SEQUENCE: 3

```
ccattcctat atggaagtaa gaccctgag agatgatcag gtagataggc tggaagtgga      60
agtgcagcga tgcatggagc ggaccagtac taatcggtcg aggacttaac caagtagagc    120
gtgagcagga gcgcttagaa accggagcat aagcgggcct gagttcgttg ccgggtttt     180 ggccaatgga ttcaggggttc ttatgtggag gtttctgcga ctgcgaacgc gtttcgatga   240
aatacactgg ttcccgacaa cacaaaaaca acaatgatag ccagttttga gagcgcaaag    300
ttctcataag tgtggtggcg atagcaagaa ggatacacct gttcccatgc c             351
```

<210> SEQ ID NO 4
<211> LENGTH: 414
<212> TYPE: DNA
<213> ORGANISM: Lactobacillus paracasei

<400> SEQUENCE: 4

```
ccattcctat atggaagtaa gaccctgag agatgatcag gtagataggc tggaagtgga      60
agtgcagcga tgcatggagc ggaccagtac taatcggtcg aggacttaac caagtaagag    120
tgtgagcagg agcggttaga aaccggagca taagcgggcc tgagcgtgat ggccgggctt    180
tggccattgc ggtcagggtc cttatgtgca ggtttctgcg actgcgaaca cgtttcgatg    240
acaagtacgt taagttcaag gcagcaatta acaatgata gctagttttg agagcgcaaa    300
gttctcataa gtgtggtggc gatagcaaga aggatacacc tgttcccatg ccgaacacag    360
aagttaagct tcttcacgcc gagagtagtt ggtgggaaac tgcctgcgag gata           414
```

<210> SEQ ID NO 5
<211> LENGTH: 338
<212> TYPE: DNA
<213> ORGANISM: Lactobacillus paracasei

<400> SEQUENCE: 5

```
ccattcctat atggaagtaa gaccctgag agatgatcag gtagataggc tggaagtgga      60
agtgcagcga tgcatggagc ggaccagtac taatcggtcg aggacttaac caagtaagcg    120
tgcaagcagg agcaggtttc tgcgactgcg aacacatttc gatgacaagt acgttaagtt    180
caaggcagca attaaacgat gatagccagt tttgagagc caaagttctc ataagtgtgg    240
tggcgatagc aagaaggata cacctgttcc catgccgaac acagaagtta agcttcttca    300
cgccgagagt agttggtggg aaactgcctg cgaggata                            338
```

<210> SEQ ID NO 6
<211> LENGTH: 317
<212> TYPE: DNA
<213> ORGANISM: Lactobacillus coryniformis ssp. coryniformis

<400> SEQUENCE: 6

```
ctcgagttga gatttcccat tcctttatgg aagtaagacc cctgagagat gatcaggtag     60
```

```
ataggttgga agtggacgtg ccgtgaggca tggagcggac caatactaat cggtcgagga      120
cttaaccaag tagcatgtac gtagtgttag tttaagggca aagaaatgaa tatccagttt      180
tgagagcgca acgttctcag aaagtggtgt ggtggcgata gcaagaagga tacacctgtt      240
cccatgtcga acacagaagt taagcttctt agcgccgaga gtagttgggg gagcacccccc     300 tgcgaggata ggacgat                                                     317

<210> SEQ ID NO 7
<211> LENGTH: 317
<212> TYPE: DNA
<213> ORGANISM: Lactobacillus coryniformis ssp. torquens

<400> SEQUENCE: 7
ctcgagatga gatttcccat tcctttatgg aagtaagacc cctgagagat gatcaggtag       60
ataggttgga agtggacgtg ccgtgaggca tggagcggac caatactaat cggtcgagga      120
cttaaccaag tagcatgtac gtggtgttag tttaagggca aagaaatgaa tatccagttt      180
tgagagcgca acgttctcag aaagtggtgt ggtggcgata gcaagaagga tacacctgtt      240
cccatgtcga acacagaagt taagcttctt agcgccgaga gtagttgggg gagcacccccc     300 tgcgaggata ggacgat                                                     317

<210> SEQ ID NO 8
<211> LENGTH: 336
<212> TYPE: DNA
<213> ORGANISM: Lactobacillus curvatus

<400> SEQUENCE: 8
acgcctcgag atgagatttc ccattccttt atggaagtaa gaccccctgaa agatgatcag      60 gtagataggc taggagtgga agtacagcga tgtatggagc ggactagtac taatcggtcg     120
aggacttaac caaaggtgca atgttaggct tttgaaatga aatattactt attatgcagt     180
tttgagagaa cgaagttctt ctcagtgcgc aagcacaaaa tagtgtggtg gcgatagcaa     240
gaaggataca cctgttccca tgtcgaacac agaagttaag cttcttagcg ccgatagtag     300
ttggtgggaa actacctgcg aggataggac gatggt                                336

<210> SEQ ID NO 9
<211> LENGTH: 335
<212> TYPE: DNA
<213> ORGANISM: Pediococcus damnosus

<400> SEQUENCE: 9
gatgagattt cccattccat ttatggaagt aagacccctg agagatgatc aggtagatag       60
gttgggagtg gaagtgtagt gatacatgga gcggaccaat actaatcggt cgaggactta     120
accacaaagt ggtgttctca agagaaggat tcgatattat ttagttttga gagaataaat     180 ttcttttcaca cgagccgcgt aagtggatcg gagaagtgtg gtgacgatag tgagaaggat     240
acacctgttc ccatgtcgaa cacagaagtt aagcttctta acgccgagag tagttggggg     300
atcgctccct gcgaggatag gacgatggtc aatag                                 335

<210> SEQ ID NO 10
<211> LENGTH: 326
<212> TYPE: DNA
<213> ORGANISM: Pediococcus inopinatus

<400> SEQUENCE: 10
```

```
agatgagatt tcccattcca tttatggaag taagacccct gagagatgat caggtagata      60
ggttgggagt ggaagtgtag tgatacatgg agcggaccaa tactaatcgg tcgaggactt     120
aaccacaaag tggtgttctc aaagagaaga tttcgatatt atttagtttt gagagaataa     180
atttctttca cacgagccgc ggaagtggat cggagaagtg tggtgacgat agtgagaagg     240
atacacctgt tcccatgtcg aacacagaag ttaagcttct taacgccgag agtagttggg     300
ggatcgctcc ctgcgaggat aggacg                                          326
```

<210> SEQ ID NO 11
<211> LENGTH: 403
<212> TYPE: DNA
<213> ORGANISM: Pectinatus cerevisiiphilus

<400> SEQUENCE: 11

```
aagtgctgaa agcatctaag cgtgaaacct gccttaagat gaggtttccc agagccgtaa      60
ggcttggaag gcaccttgaa taagacgagg tagataggcc gggagtagaa gtacagtaat     120
gtacgaagcg gactggtact aataagccga gagcttaact taaaatcatc gaaaaaaatg     180
tttggtctga gatttcttct gtgaagtttt gagtgtgcaa gacactctgg ttgaagggca     240
gggaacgtga gagcgtaaaa ctgcggactt tggctcaaag agttaaagca tctggtgacg     300
atacctggat ggatccacct gttcccattc cgaacacagt agttaagcat ccacaggctg     360
aaggtacttg ggggcgacc ccctgggaaa ataggacact gcc                        403
```

<210> SEQ ID NO 12
<211> LENGTH: 434
<212> TYPE: DNA
<213> ORGANISM: Pectinatus frisingensis

<400> SEQUENCE: 12

```
aagtgctgaa agcatctaag cgtgaaacca gctttaagat gaggtttccc agaacgcaag      60
tttggaaggc accttgaaga agacgaggta gataggccgg gagtggaagt atggtgacat     120
atgaagcgga ctggtactaa taagccgaga gcttaacttg atttcatcaa aaagagaaa     180 tgtttggtca gagattttct tctgtgaagt tttgagtgtg caagaacact cgagagtata     240
taggtaaagg aaaagcagca gataagtttc ctggttactg tatataccgg ctgaggtgct     300
gaggcactga aggccagaac atctggtggc gatacctgga tggatccacc tgttcccatt     360
ccgaacacag tagttaagca tccacaggcc gaaggtactt gggggcagc cccctgcgaa     420 aataggacac gcc                                                        434
```

<210> SEQ ID NO 13
<211> LENGTH: 641
<212> TYPE: DNA
<213> ORGANISM: Pectinatus spec. DSM20764

<400> SEQUENCE: 13

```
aagtgctgaa agcatctaag cgtgaaacct gccttaagat gaggtttccc agagccgtaa      60
ggcttggaag gcaccttgaa gatgacgagg tagataggcc gggagtagaa gtatggtgac     120
atacgaagcg gactggtact aataagccga gagcttaact taatttcatc tataaatgtt     180
tggtcctgat ttcttctgtg aagttttgag tgtgcaagat cactcatgaa agtatatagg     240
taaagggaaa gcagcagatt agttcctggt ttactttata tatgagcact aaggtgcaga     300
aaagaacgtt tgaggaaacg cggcgttcgt aaactcactt tgcgtgctga ttatctcaat     360
gctaaagcat taagataatt ttagaggaaa cgcgcgttca ctagcgttca ctctgcgtac     420
```

```
tttatttcta agtgctgaag cactaagaag ggcaaggaaa cgcgtcgttc gcgatgctca        480 cttttgcgtac ttcatctcta gactgctaaa gcagtaagat ctgaagcatc tggtggcgat        540
acctggatgg atccacctgt tcccattccg aacacagtag ttaagcatcc acaggccgaa        600
ggtacttggg gggcagcccc ctgcgagagt aggacatcgc c                             641

<210> SEQ ID NO 14
<211> LENGTH: 495
<212> TYPE: DNA
<213> ORGANISM: Pectinatus spec. DSM20764

<400> SEQUENCE: 14
aagtgctgaa agcatctaag cgtgaaacct gccttaagat gaggtttccc agagccgtaa         60
ggcttggaag gcaccttgaa gatgacgagg tagataggcc gggagtagaa gtatggtgac        120
atacgaagcg gactggtact aataagccga gagcttaact taatttcatc tataaatgtt        180
tggtcctgat ttcttctgtg aagttttgag tgtgcaagat cactcatgaa agtatatagg        240
taaaggggaa gcagattagt tcctggttta ctttatatat gagcactaag gtgcagaaaa        300
gaacgtctaa ggaaacgcgg cgttcgtagg ctcactctgc gtacttcatc tctagactgc        360
taaagcagta agatctgaag catctggtgg cgatacctgg atggatccac ctgttcccat        420
tccgaacaca gtagttaagc atccacaggc cgaaggtact ggggggcag ccccctgcga        480 aagtaggaca ccgcc                                                           495

<210> SEQ ID NO 15
<211> LENGTH: 546
<212> TYPE: DNA
<213> ORGANISM: Megasphaera cerevisiae

<400> SEQUENCE: 15
gcatctaagc gtgaaaccag cctagagatg aggtttctca ttacgaaagt aagtaaggtc         60
ccatgaagac gacatggtag ataggccggg agtggacgta cagtaatgta tggagcggac        120
cggtactaat agaccgagga cttgacttaa gcagggaacc cattttaaag aagcgaagcg        180
acgcataaaa tggagtgagt cgcttatacc gaatcgcaga ttcggtaaag cagcggagaa        240
taccaatgca gcggcaacac cagttagcat aaactaagcg gattcggagt gggtgaggga        300
gtttcgtagc agcgtaggct aacccaacca ccgctttcga agaaggcgaa tggtttgaaa        360
aagagtacat gcgaagaaac gacgaaagac tcacaaccaa aacatacaaa ctaagtagat        420
gacattagag tcacaccgat tgttaagatc cgaaatactt ttcgatgtag ttgtcaggat        480
acgaatcctg aaacgaattc agtggtgatg gctgcaggga tccacctgtt cccataccga        540
acacag                                                                     546

<210> SEQ ID NO 16
<211> LENGTH: 306
<212> TYPE: DNA
<213> ORGANISM: Megasphaera cerevisiae

<400> SEQUENCE: 16
gcatctaacc gtgaaaccag cctagagatg aggtttctca ttacgaaagt aagtaaggtc         60
ccatgaagac gacatggtag ataggccggg agtggacgta cagtaatgta tggagcggac        120
cggtactaat agaccgagga cttgacttaa gcaaagaagc aatagaaaga accatgtaga        180
tggtgtaaga gttagacggg tagttaaggt ccgaaatact tttcgatgta gttgtcagga        240
```

| tacgaatcct gaaacgaatt cagtggtgat ggctgcaggg accacctgtt cccataccga | 300 |
| acacag | 306 |

<210> SEQ ID NO 17
<211> LENGTH: 449
<212> TYPE: DNA
<213> ORGANISM: Selenomonas lacticifex

<400> SEQUENCE: 17

| aagtgctgaa agcatctagg cgtgaagcct gtcccgagat gaagtatctc atggagtaat | 60 |
| ccagtaagat tccttgaaga agacaaggta gataggttgg gagtgtaagc atcgtaaggt | 120 |
| gttcagcgga ccaatactaa taaatcgagg gcttaacttt acagacctgt ccaagaagcg | 180 |
| aagcggattg ggtaacaggt cgtatgcgaa aacatcccaa gaatcgagtc cgaagggcga | 240 |
| agatgattgg cagatgttga ccgctaataa tctagaatgt ttcgatacaa tttttcttct | 300 |
| gtatagtttt gagtggacat cgttcattca ataatatcca gtgacgatag ctgagtggta | 360 |
| ccacctgttc ccataccgaa cacagtagtt aagcactcat acgccgaaag tacttgtctg | 420 |
| gaaacgggct gcgagaatag gacgtcgcc | 449 |

<210> SEQ ID NO 18
<211> LENGTH: 343
<212> TYPE: DNA
<213> ORGANISM: Selenomonas lacticifex

<400> SEQUENCE: 18

| aagtgctgaa agcatctaag cgtgaagcct gtcccgagat gaagtatctc atggagtaat | 60 |
| ccagtaagat tccttgaaga agacaaggta gataggttgg gagtgtaagc atcgtaaggt | 120 |
| gttcagcgga ccaatactaa taaatcgagg gcttatctta ataatctaga atgtttcgat | 180 |
| acaattttc ttctgtatag ttttgagtgg acatggttca ttcaataata tccagtgacg | 240 |
| atagctgagt ggtaccacct gttcccatac cgaacacagt agttaagcac tcatacgccg | 300 |
| aaagtacttg tctggaaacg ggctgcgaaa ataggacgcc gcc | 343 |

<210> SEQ ID NO 19
<211> LENGTH: 395
<212> TYPE: DNA
<213> ORGANISM: Zymophilus raffinosivorans

<400> SEQUENCE: 19

| aagtgctgaa agcatctaag cgtgaaacca gccttaagat gaggtttctc acagagcaat | 60 |
| ctggtaagac cccttgaaga agacaaggta gataggtcgg gagtggaagc gcagtaatgt | 120 |
| gtgcagcgga ccgatactaa taggtcgagg gcttgactta aagccagaac gaaaactaaa | 180 |
| atgcgaacat ttctttcttc tgtatagttt tgagagaaca aactcttaag atggagtagt | 240 |
| ctgaggcgaa agcggaaggc agcgatatct aaaaaaagaa tatctggtag tgatagccaa | 300 |
| gtggacccac ctgttcccat accgaacaca gtagttaagc acttgaacgt cgaaagtact | 360 |
| tgggtggaaa cgccctgcga aaataggaca ccgcc | 395 |

<210> SEQ ID NO 20
<211> LENGTH: 395
<212> TYPE: DNA
<213> ORGANISM: Zymophilus paucivorans

<400> SEQUENCE: 20

| aagtgctgaa agcatctaag cgtgaaacca gccttaagat gaggtttctc acagagcaat | 60 |

```
ctggtaagac cccttgaaga agacaaggta gataggtcgg gagtggaagc gcagtaatgt    120
gtgtagcgga ccgatactaa taggtcgagg gcttgactta aagccagaac gaattctaaa    180
atgcgaacat ttctttcttc tgtatagttt tgagagaaca gactcttaag atgagcagtc    240
tgaggcgaaa gctaaaggca gcgatatcta aaaaaaagaa tatctggtag tgatagccaa    300
gtggacccac ctgttcccat accgaacaca gtagttaagc acttgaacgt cgaaagtact    360
tgggtggaaa cgccctggga aaataggaca ccgcc                               395
```

<210> SEQ ID NO 21
<211> LENGTH: 21
<212> TYPE: DNA
<213> ORGANISM: Artificial Sequence
<220> FEATURE:
<223> OTHER INFORMATION: Description of the artifical sequence: specific
      sequence for Lactobacillus brevis

<400> SEQUENCE: 21

```
ccaagtcaac aacgtagttg t                                               21
```

<210> SEQ ID NO 22
<211> LENGTH: 23
<212> TYPE: DNA
<213> ORGANISM: Artificial Sequence
<220> FEATURE:
<223> OTHER INFORMATION: Description of the artifical sequence: specific
      sequence for Lactobacillus lindneri

<400> SEQUENCE: 22

```
gacacagggt taaatcaaag ttg                                             23
```

<210> SEQ ID NO 23
<211> LENGTH: 20
<212> TYPE: DNA
<213> ORGANISM: Artificial Sequence
<220> FEATURE:
<223> OTHER INFORMATION: Description of the artifical sequence: specific
      sequence for Lactobacillus casei and Lactobacillus
      paracasei

<400> SEQUENCE: 23

```
aggtttctgc gactgcgaac                                                 20
```

<210> SEQ ID NO 24
<211> LENGTH: 25
<212> TYPE: DNA
<213> ORGANISM: Artificial Sequence
<220> FEATURE:
<223> OTHER INFORMATION: Description of the artifical sequence: specific
      sequence for Lactobacillus coryniformis

<400> SEQUENCE: 24

```
atgtacgtag tgttagttta agggc                                           25
```

<210> SEQ ID NO 25
<211> LENGTH: 20
<212> TYPE: DNA
<213> ORGANISM: Artificial Sequence
<220> FEATURE:
<223> OTHER INFORMATION: Description of the artifical sequence: specific
      sequence for Lactobacillus curvatus

<400> SEQUENCE: 25

```
cttctcagtg cgcaagcaca                                                 20
```

<210> SEQ ID NO 26
<211> LENGTH: 22
<212> TYPE: DNA
<213> ORGANISM: Artificial Sequence
<220> FEATURE:
<223> OTHER INFORMATION: Description of the artifical sequence: specific
      sequence for Pediococcus damnosus

<400> SEQUENCE: 26
gtgttctcaa gagaaggatt cg                                               22

<210> SEQ ID NO 27
<211> LENGTH: 27
<212> TYPE: DNA
<213> ORGANISM: Artificial Sequence
<220> FEATURE:
<223> OTHER INFORMATION: Description of the artifical sequence: specific
      sequence for Pediococcus inopinatus

<400> SEQUENCE: 27
gttctcaaag agaagatttc gatatta                                          27

<210> SEQ ID NO 28
<211> LENGTH: 23
<212> TYPE: DNA
<213> ORGANISM: Artificial Sequence
<220> FEATURE:
<223> OTHER INFORMATION: Description of the artifical sequence: specific
      sequence for Pectinatus cerevisiiphilus

<400> SEQUENCE: 28
tgagagcgta aaactgcgga ctt                                              23

<210> SEQ ID NO 29
<211> LENGTH: 22
<212> TYPE: DNA
<213> ORGANISM: Artificial Sequence
<220> FEATURE:
<223> OTHER INFORMATION: Description of the artifical sequence: specific
      sequence for Pectinatus frisingensis

<400> SEQUENCE: 29
cagataagtt tcctggttac tg                                               22

<210> SEQ ID NO 30
<211> LENGTH: 23
<212> TYPE: DNA
<213> ORGANISM: Artificial Sequence
<220> FEATURE:
<223> OTHER INFORMATION: Description of the artifical sequence: specific
      sequence for Pectinatus spec. DSM 20764

<400> SEQUENCE: 30
cactaaggtg cagaaaagaa cgt                                              23

<210> SEQ ID NO 31
<211> LENGTH: 26
<212> TYPE: DNA
<213> ORGANISM: Artificial Sequence
<220> FEATURE:
<223> OTHER INFORMATION: Description of the artifical sequence: specific
      sequence for Megasphaera cerevisiae

<400> SEQUENCE: 31
cttttcgatg tagttgtcag gatacg                                           26

<210> SEQ ID NO 32
<211> LENGTH: 25
<212> TYPE: DNA
<213> ORGANISM: Artificial Sequence
<220> FEATURE:
<223> OTHER INFORMATION: Description of the artifical sequence: specific
      sequence for Selenomonas lacticifex

<400> SEQUENCE: 32
gttcattcaa taatatccag tgacg                                          25

<210> SEQ ID NO 33
<211> LENGTH: 23
<212> TYPE: DNA
<213> ORGANISM: Artificial Sequence
<220> FEATURE:
<223> OTHER INFORMATION: Description of the artifical sequence: specific
      sequence for Zymophilus raffinosivorans

<400> SEQUENCE: 33
aactcttaag atggagyagt ctg                                            23

<210> SEQ ID NO 34
<211> LENGTH: 22
<212> TYPE: DNA
<213> ORGANISM: Artificial Sequence
<220> FEATURE:
<223> OTHER INFORMATION: Description of the artifical sequence: specific
      sequence for Zymophilus paucivorans

<400> SEQUENCE: 34
actcttaaga tgagcagtct ga                                             22

<210> SEQ ID NO 35
<211> LENGTH: 21
<212> TYPE: DNA
<213> ORGANISM: Artificial Sequence
<220> FEATURE:
<223> OTHER INFORMATION: Description of the artifical sequence: specific
      sequence for the genus Pediococcus

<400> SEQUENCE: 35
agtstagtga tacatggagc g                                              21

<210> SEQ ID NO 36
<211> LENGTH: 22
<212> TYPE: DNA
<213> ORGANISM: Artificial Sequence
<220> FEATURE:
<223> OTHER INFORMATION: Description of the artifical sequence: specific
      sequence for the genus Pectinatus

<400> SEQUENCE: 36
gtgaagtttt gagtgtgcaa ga                                             22

<210> SEQ ID NO 37
<211> LENGTH: 22
<212> TYPE: DNA
<213> ORGANISM: Artificial Sequence
<220> FEATURE:
<223> OTHER INFORMATION: Description of the artifical sequence: specific
      sequence for the genus Megasphaera

<400> SEQUENCE: 37
gaccgaggac ttgacttaag ca                                             22

<210> SEQ ID NO 38

```
<211> LENGTH: 20
<212> TYPE: DNA
<213> ORGANISM: Artificial Sequence
<220> FEATURE:
<223> OTHER INFORMATION: Description of the artifical sequence: specific
      sequence for the genus Selenomonas

<400> SEQUENCE: 38
tccagtgacg atagctgagt                                               20

<210> SEQ ID NO 39
<211> LENGTH: 25
<212> TYPE: DNA
<213> ORGANISM: Artificial Sequence
<220> FEATURE:
<223> OTHER INFORMATION: Description of the artifical sequence: specific
      sequence for the genus Zymophilus

<400> SEQUENCE: 39
aagaatatct ggtagtgata gccaa                                         25

<210> SEQ ID NO 40
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 40
gtcgtgagac agttcggtc                                                19

<210> SEQ ID NO 41
<211> LENGTH: 21
<212> TYPE: DNA
<213> ORGANISM: Artificial Sequence
<220> FEATURE:
<223> OTHER INFORMATION: Description of the artifical sequence:
      consensus sequence

<400> SEQUENCE: 41
cytagtacga gaggaccggr r                                             21

<210> SEQ ID NO 42
<211> LENGTH: 21
<212> TYPE: DNA
<213> ORGANISM: Artificial Sequence
<220> FEATURE:
<223> OTHER INFORMATION: Description of the artifical sequence:
      consensus sequence

<400> SEQUENCE: 42
gctaccctgg ggataacagg c                                             21

<210> SEQ ID NO 43
<211> LENGTH: 21
<212> TYPE: DNA
<213> ORGANISM: Artificial Sequence
<220> FEATURE:
<223> OTHER INFORMATION: Description of the artifical sequence:
      consensus sequence

<400> SEQUENCE: 43
atcgacgggg aggtttssca c                                             21

<210> SEQ ID NO 44
<211> LENGTH: 20
```

<210> SEQ ID NO 44
<211> LENGTH: 20
<212> TYPE: DNA
<213> ORGANISM: Artificial Sequence
<220> FEATURE:
<223> OTHER INFORMATION: Description of the artifical sequence:
      consensus sequence

<400> SEQUENCE: 44
cacctcgatg tcggctcrtc                                              20

<210> SEQ ID NO 45
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 45
ccaagggttg ggctgttc                                                18

<210> SEQ ID NO 46
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 46
aagggccatc rctcaacgg                                               19

<210> SEQ ID NO 47
<211> LENGTH: 20
<212> TYPE: DNA
<213> ORGANISM: Artificial Sequence
<220> FEATURE:
<223> OTHER INFORMATION: Description of the artifical sequence:
      consensus sequence

<400> SEQUENCE: 47
aagtgctgaa agcatctaag                                              20

<210> SEQ ID NO 48
<211> LENGTH: 23
<212> TYPE: DNA
<213> ORGANISM: Artificial Sequence
<220> FEATURE:
<223> OTHER INFORMATION: Description of the artifical sequence:
      consensus sequence
<221> NAME/KEY: misc_feature
<222> LOCATION: (9)..(10)
<223> OTHER INFORMATION: "n" is inosine

<400> SEQUENCE: 48
tgtgttcgnn atgggaacag gtg                                          23

<210> SEQ ID NO 49
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 49
tgtgttcgga atgggaacag gtg                                          23

<210> SEQ ID NO 50
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 50
tgtgttcgaa atgggaacag gtg                                              23

<210> SEQ ID NO 51
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 51
tgtgttcggt atgggaacag gtg                                              23

<210> SEQ ID NO 52
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 52
tgtgttcgat atgggaacag gtg                                              23

<210> SEQ ID NO 53
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 53
tgtgttcggc atgggaacag gtg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of the artifical sequence:
      consensus sequence

<400> SEQUENCE: 54
tgtgttcgac atgggaacag gtg                                              23

<210> SEQ ID NO 55
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 55
ggcrrygtcc taytytcsc                                                   19

<210> SEQ ID NO 56

-continued

```
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 56
ggcagtgtcc tactttccc                                              19

<210> SEQ ID NO 57
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 57
ggcagcgtcc tactttcgc                                              19

<210> SEQ ID NO 58
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 58
ggcagtgtcc tactttcgc                                              19

<210> SEQ ID NO 59
<211> LENGTH: 19
<212> TYPE: DNA
<213> ORGANISM: Artificial Sequence
<220> FEATURE:
<223> OTHER INFORMATION: Description of the artifical sequence:
      consensus sequence

<400> SEQUENCE: 59
ggcagcgtcc tactttccc                                              19

<210> SEQ ID NO 60
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 60
gyttmrcttc yrdgttcg                                               18

<210> SEQ ID NO 61
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 61
gcttaacttc cgtgttcg                                               18

<210> SEQ ID NO 62
<211> LENGTH: 18
```

```
<212> TYPE: DNA
<213> ORGANISM: Artificial Sequence
<220> FEATURE:
<223> OTHER INFORMATION: Description of the artifical sequence:
      consensus sequence

<400> SEQUENCE: 62
gcttaacttc tatgttcg                                                 18

<210> SEQ ID NO 63
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 63
gcttaacttc tgtgttcg                                                 18

<210> SEQ ID NO 64
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 64
gcttaacttc catgttcg                                                 18

<210> SEQ ID NO 65
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 65
gcttaacttc cgggttcg                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 66
gcttaacttc taggttcg                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 67
gcttaacttc tgggttcg                                                 18

<210> SEQ ID NO 68
<211> LENGTH: 18
<212> TYPE: DNA
```

```
<213> ORGANISM: Artificial Sequence
<220> FEATURE:
<223> OTHER INFORMATION: Description of the artifical sequence:
      consensus sequence

<400> SEQUENCE: 68
gcttaacttc caggttcg                                              18

<210> SEQ ID NO 69
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 69
gcttaacttc cgagttcg                                              18

<210> SEQ ID NO 70
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 70
gcttaacttc taagttcg                                              18

<210> SEQ ID NO 71
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 71
gcttaacttc tgagttcg                                              18

<210> SEQ ID NO 72
<211> LENGTH: 18
<212> TYPE: DNA
<213> ORGANISM: Artificial Sequence
<220> FEATURE:
<223> OTHER INFORMATION: Description of the artifical sequence:
      consensus sequence

<400> SEQUENCE: 72
gcttaacttc caagttcg                                              18

<210> SEQ ID NO 73
<211> LENGTH: 25
<212> TYPE: DNA
<213> ORGANISM: Artificial Sequence
<220> FEATURE:
<223> OTHER INFORMATION: Description of the artifical sequence:
      specific sequence for Lactobacillus brevis

<400> SEQUENCE: 73
tcgagaataa ttgaataata tctag                                      25

<210> SEQ ID NO 74
<211> LENGTH: 20
<212> TYPE: DNA
<213> ORGANISM: Artificial Sequence
```

```
<220> FEATURE:
<223> OTHER INFORMATION: Description of the artifical sequence: specific
      sequence for Lactobacillus brevis

<400> SEQUENCE: 74
gagggaagaa gttctcttat                                                    20

<210> SEQ ID NO 75
<211> LENGTH: 23
<212> TYPE: DNA
<213> ORGANISM: Artificial Sequence
<220> FEATURE:
<223> OTHER INFORMATION: Description of the artifical sequence: specific
      sequence for Lactobacillus lindneri

<400> SEQUENCE: 75
aacagagaag atattatcta gtt                                                23

<210> SEQ ID NO 76
<211> LENGTH: 42
<212> TYPE: DNA
<213> ORGANISM: Artificial Sequence
<220> FEATURE:
<223> OTHER INFORMATION: Description of the artifical sequence: specific
      sequence for Lactobacillus lindneri

<400> SEQUENCE: 76
ttgagagaac gaagttcgct caggcttatg aaaaataagc at                           42

<210> SEQ ID NO 77
<211> LENGTH: 45
<212> TYPE: DNA
<213> ORGANISM: Artificial Sequence
<220> FEATURE:
<223> OTHER INFORMATION: Description of the artifical sequence: specific
      sequence for Lactobacillus casei

<400> SEQUENCE: 77
ttcgttggcc gggttttggc caatggattc agggttctta tgtgg                        45

<210> SEQ ID NO 78
<211> LENGTH: 58
<212> TYPE: DNA
<213> ORGANISM: Artificial Sequence
<220> FEATURE:
<223> OTHER INFORMATION: Description of the artifical sequence: specific
      sequence for Lactobacillus casei

<400> SEQUENCE: 78
gcgtttcgat gaaatacact ggttcccgac aacacaaaaa caacaatgat agccagtt          58

<210> SEQ ID NO 79
<211> LENGTH: 29
<212> TYPE: DNA
<213> ORGANISM: Artificial Sequence
<220> FEATURE:
<223> OTHER INFORMATION: Description of the artifical sequence: specific
      sequence for Lactobacillus casei and Lactobacillus
      paracasei

<400> SEQUENCE: 79
ttagaaaccg gagcataagc gggcctgag                                          29

<210> SEQ ID NO 80
<211> LENGTH: 46
<212> TYPE: DNA
<213> ORGANISM: Artificial Sequence
```

```
<220> FEATURE:
<223> OTHER INFORMATION: Description of the artifical sequence: specific
      sequence for Lactobacillus paracasei

<400> SEQUENCE: 80
gcgtgatggc cgggctttgg ccattgcggt cagggtcctt atgtgc                46

<210> SEQ ID NO 81
<211> LENGTH: 46
<212> TYPE: DNA
<213> ORGANISM: Artificial Sequence
<220> FEATURE:
<223> OTHER INFORMATION: Description of the artifical sequence: specific
      sequence for Lactobacillus paracasei

<400> SEQUENCE: 81
caagtacgtt aagttcaagg cagcaattaa acaatgatag ctagtt                46

<210> SEQ ID NO 82
<211> LENGTH: 44
<212> TYPE: DNA
<213> ORGANISM: Artificial Sequence
<220> FEATURE:
<223> OTHER INFORMATION: Description of the artifical sequence: specific
      sequence for Lactobacillus coryniformis

<400> SEQUENCE: 82
aaagaaatga atatccagtt ttgagagcgc aacgttctca gaaa                  44

<210> SEQ ID NO 83
<211> LENGTH: 48
<212> TYPE: DNA
<213> ORGANISM: Artificial Sequence
<220> FEATURE:
<223> OTHER INFORMATION: Description of the artifical sequence: specific
      sequence for Lactobacillus curvatus

<400> SEQUENCE: 83
aggtgcaatg ttaggctttt gaaatgaaat attacttatt atgcagtt              48

<210> SEQ ID NO 84
<211> LENGTH: 22
<212> TYPE: DNA
<213> ORGANISM: Artificial Sequence
<220> FEATURE:
<223> OTHER INFORMATION: Description of the artifical sequence: specific
      sequence for Pediococcus damnosus

<400> SEQUENCE: 84
gccgcgtaag tggatcggag aa                                          22

<210> SEQ ID NO 85
<211> LENGTH: 22
<212> TYPE: DNA
<213> ORGANISM: Artificial Sequence
<220> FEATURE:
<223> OTHER INFORMATION: Description of the artifical sequence: specific
      sequence for Pediococcus inopinatus

<400> SEQUENCE: 85
gccgcggaag tggatcggag aa                                          22

<210> SEQ ID NO 86
<211> LENGTH: 25
<212> TYPE: DNA
<213> ORGANISM: Artificial Sequence
```

```
<220> FEATURE:
<223> OTHER INFORMATION: Description of the artifical sequence: sequence
      for the detection of Pediococcus damnosus, Pediococcus inopinatus
      and Pediococcus parvulus

<400> SEQUENCE: 86
gagagaataa atttctttca cacga                                              25

<210> SEQ ID NO 87
<211> LENGTH: 39
<212> TYPE: DNA
<213> ORGANISM: Artificial Sequence
<220> FEATURE:
<223> OTHER INFORMATION: Description of the artifical sequence: specific
      sequence for Pectinatus cerevisiiphilus

<400> SEQUENCE: 87
aaaatcatcg aaaaaaatgt ttggtctgag atttcttct                               39

<210> SEQ ID NO 88
<211> LENGTH: 25
<212> TYPE: DNA
<213> ORGANISM: Artificial Sequence
<220> FEATURE:
<223> OTHER INFORMATION: Description of the artifical sequence: specific
      sequence for Pectinatus cerevisiiphilus

<400> SEQUENCE: 88
cactctggtt gaagggcagg gaacg                                              25

<210> SEQ ID NO 89
<211> LENGTH: 39
<212> TYPE: DNA
<213> ORGANISM: Artificial Sequence
<220> FEATURE:
<223> OTHER INFORMATION: Description of the artifical sequence: specific
      sequence for Pectinatus frisingensis

<400> SEQUENCE: 89
gatttcatca aaaagagaa atgtttggtc agagatttt                                39

<210> SEQ ID NO 90
<211> LENGTH: 33
<212> TYPE: DNA
<213> ORGANISM: Artificial Sequence
<220> FEATURE:
<223> OTHER INFORMATION: Description of the artifical sequence: specific
      sequence for Pectinatus frisingensis

<400> SEQUENCE: 90
tatataccgg ctgaggtgct gaggcactga agg                                     33

<210> SEQ ID NO 91
<211> LENGTH: 36
<212> TYPE: DNA
<213> ORGANISM: Artificial Sequence
<220> FEATURE:
<223> OTHER INFORMATION: Description of the artifical sequence: specific
      sequence for Pectinatus spec. DSM 20764

<400> SEQUENCE: 91
aatttcatct ataaatgttt ggtcctgatt tcttct                                  36

<210> SEQ ID NO 92
<211> LENGTH: 54
<212> TYPE: DNA
<213> ORGANISM: Artificial Sequence
```

```
<220> FEATURE:
<223> OTHER INFORMATION: Description of the artifical sequence: specific
      sequence for Pectinatus spec. DSM 20764

<400> SEQUENCE: 92
agattagttc ctggtttact ttatatatga gcactaaggt gcagaaaaga acgt            54

<210> SEQ ID NO 93
<211> LENGTH: 20
<212> TYPE: DNA
<213> ORGANISM: Artificial Sequence
<220> FEATURE:
<223> OTHER INFORMATION: Description of the artifical sequence: specific
      sequence for Pectinatus spec. DSM 20764

<400> SEQUENCE: 93
aggaaacgcg gcgttcgtaa                                                  20

<210> SEQ ID NO 94
<211> LENGTH: 56
<212> TYPE: DNA
<213> ORGANISM: Artificial Sequence
<220> FEATURE:
<223> OTHER INFORMATION: Description of the artifical sequence: specific
      sequence for Selenomonas lacticifex

<400> SEQUENCE: 94
taataatcta gaatgtttcg atacaatttt tcttctgtat agttttgagt ggacat          56

<210> SEQ ID NO 95
<211> LENGTH: 24
<212> TYPE: DNA
<213> ORGANISM: Artificial Sequence
<220> FEATURE:
<223> OTHER INFORMATION: Description of the artifical sequence: specific
      sequence for Zymophilus raffinosivorans

<400> SEQUENCE: 95
gaggcgaaag cggaaggcag cgat                                             24

<210> SEQ ID NO 96
<211> LENGTH: 24
<212> TYPE: DNA
<213> ORGANISM: Artificial Sequence
<220> FEATURE:
<223> OTHER INFORMATION: Description of the artifical sequence: specific
      sequence for Zymophilus paucivorans

<400> SEQUENCE: 96
gaggcgaaag ctaaaggcag cgat                                             24

<210> SEQ ID NO 97
<211> LENGTH: 37
<212> TYPE: DNA
<213> ORGANISM: Artificial Sequence
<220> FEATURE:
<223> OTHER INFORMATION: Description of the artifical sequence: specific
      sequence for Megasphaera cerevisiae

<400> SEQUENCE: 97
aatcctgaaa cgaattcagt ggtgatggct gcaggga                               37

<210> SEQ ID NO 98
<211> LENGTH: 20
<212> TYPE: DNA
<213> ORGANISM: Artificial Sequence
```

```
<220> FEATURE:
<223> OTHER INFORMATION: Description of the artifical sequence: sequence
      for detection of bacteria of the family Lactobacillaceae that are
      relevant to brewing

<400> SEQUENCE: 98
tatggaagta agacccctga                                                    20

<210> SEQ ID NO 99
<211> LENGTH: 21
<212> TYPE: DNA
<213> ORGANISM: Artificial Sequence
<220> FEATURE:
<223> OTHER INFORMATION: Description of the artifical sequence: sequence
      for detection of bacteria of the family Lactobacillaceae that are
      relevant to brewing

<400> SEQUENCE: 99
agatgatcag gtagataggc t                                                  21

<210> SEQ ID NO 100
<211> LENGTH: 21
<212> TYPE: DNA
<213> ORGANISM: Artificial Sequence
<220> FEATURE:
<223> OTHER INFORMATION: Description of the artifical sequence: sequence
      for detection of bacteria of the family Lactobacillaceae that are
      relevant to brewing

<400> SEQUENCE: 100
agatgatcag gtcgataggt t                                                  21

<210> SEQ ID NO 101
<211> LENGTH: 21
<212> TYPE: DNA
<213> ORGANISM: Artificial Sequence
<220> FEATURE:
<223> OTHER INFORMATION: Description of the artifical sequence: sequence
      for detection of bacteria of the family Lactobacillaceae that are
      relevant to brewing

<400> SEQUENCE: 101
agatgatcag gtagataggt t                                                  21

<210> SEQ ID NO 102
<211> LENGTH: 25
<212> TYPE: DNA
<213> ORGANISM: Artificial Sequence
<220> FEATURE:
<223> OTHER INFORMATION: Description of the artifical sequence: sequence
      for detection of bacteria of the family Lactobacillaceae that are
      relevant to brewing

<400> SEQUENCE: 102
tactaatcgg tcgaggactt aacca                                              25

<210> SEQ ID NO 103
<211> LENGTH: 26
<212> TYPE: DNA
<213> ORGANISM: Artificial Sequence
<220> FEATURE:
<223> OTHER INFORMATION: Description of the artifical sequence: sequence
      for detection of bacteria of the family Lactobacillaceae that are
      relevant to brewing

<400> SEQUENCE: 103
atactaatca gtcgaggact taacca                                             26
```

-continued

```
<210> SEQ ID NO 104
<211> LENGTH: 32
<212> TYPE: DNA
<213> ORGANISM: Artificial Sequence
<220> FEATURE:
<223> OTHER INFORMATION: Description of the artifical sequence: specific
      sequence for the genus Pectinatus

<400> SEQUENCE: 104
gaagcggact ggtactaata agccgagagc tt                                   32

<210> SEQ ID NO 105
<211> LENGTH: 32
<212> TYPE: DNA
<213> ORGANISM: Artificial Sequence
<220> FEATURE:
<223> OTHER INFORMATION: Description of the artifical sequence: specific
      sequence for the genus Selenomonas

<400> SEQUENCE: 105
cagcggacca atactaataa atcgagggct ta                                   32

<210> SEQ ID NO 106
<211> LENGTH: 38
<212> TYPE: DNA
<213> ORGANISM: Artificial Sequence
<220> FEATURE:
<223> OTHER INFORMATION: Description of the artifical sequence: specific
      sequence for the genus Zymophilus

<400> SEQUENCE: 106
agcggaccga tactaatagg tcgagggctt gacttaaa                             38

<210> SEQ ID NO 107
<211> LENGTH: 32
<212> TYPE: DNA
<213> ORGANISM: Artificial Sequence
<220> FEATURE:
<223> OTHER INFORMATION: Description of the artifical sequence: specific
      sequence for the genus Megasphaera

<400> SEQUENCE: 107
ggagcggacc ggtactaata gaccgaggac tt                                   32
```

The invention claimed is:

1. A method for the detection of *L. brevis* in a sample, which comprises the following steps:
   (a) bringing the sample into contact with a combination of at least two first nucleic acid molecules (primers), which hybridize with a region of a *L. brevis* nucleic acid, wherein each of the at least two first nucleic acid molecules is selected from the group consisting of:
      (i) SEQ ID NO 1, 21, 73 or 74, or a fragment thereof of 15 to 30 nucleotides,
      (ii) a nucleic acid which specifically hybridizes under stringent conditions with SEQ ID NO: 1, 21, 73, or 74, wherein the stringent conditions comprise hybridizing the nucleic acids at 50° C. with a hybridization solution consisting of 2.5×SSC, 2× Denhardts solution, 10 mM TRIS, 1 mM EDTA pH 7.5, and 1 minute washings in 0.1×SSC to 1.0×SSC, 2× Denhardts solution, 10 mM TRIS, 1 mM EDTA pH 7.5 at 20–50° C. repeated four times, and
      (iii) a nucleic acid which is the complement of a nucleic acid according to (i) and (ii),
   (b) amplifying the *L. brevis* nucleic acid or a portion thereof to produce at least one amplification fragment;
   (c) contacting the amplification fragments obtained in step (b) with at least one second nucleic acid molecule (probe), which specifically hybridizes with at least one amplification fragment that comprises a sequence of the microbial nucleic acid specific for *L. brevis*, wherein the at least one second nucleic acid molecule is selected from the group consisting of:
      (i) a nucleic acid sequence consisting of SEQ ID NO: 21, 73 or 74, or a fragment thereof, said fragment consisting of at least 15 nucleotides,
      (ii) a nucleic acid of (i) which is modified such that one or two nucleotides in 10 consecutive nucleotides of (i) are replaced by nucleotides which do not naturally occur in bacteria,
      (iii) a nucleic acid which is the complement of a nucleic acid according to (i) or (ii) and (d) detecting at least one hybrid nucleic acid which consists of an amplification fragment and a second nucleic acid molecule contacted in step (c), whereupon *L. brevis* is detected in a sample.

2. The method according to claim 1, characterized in that the amplification comprises a polymerase chain reaction (PCR).

3. The method according to claim 1, characterized in that the amplification comprises a ligase chain reaction.

4. The method according to claim 1, characterized in that the amplification comprises an isothermal nucleic acid amplification.

5. The method according to claim 1, characterized in that the second nucleic acid molecule is modified or labeled to produce a detectable signal, wherein the modification or label is selected from the group consisting of (i) radioactive groups, (ii) colored groups, (iii) fluorescent groups, (iv) groups for immobilization on a solid phase and (v) groups which allow an indirect or direct reaction by means of antibodies, antigens, enzymes and/or substances with affinity for enzymes or enzyme complexes.

* * * * *